US012616676B2

(12) United States Patent
Gao

(10) Patent No.: US 12,616,676 B2
(45) **Date of Patent: *May 5, 2026**

(54) PREPARATION METHOD AND USE OF MODIFIED HYDROPHOBIC EXCIPIENT

(71) Applicant: ZHEJIANG ZHIDA PHARMACEUTICAL CO., LTD., Shaoxing (CN)

(72) Inventor: Xiang Gao, Shaoxing (CN)

(73) Assignee: ZHEJIANG ZHIDA PHARMACEUTICAL CO., LTD., Shaoxing (CN)

( * ) Notice: Subject to any disclaimer, the term of this patent is extended or adjusted under 35 U.S.C. 154(b) by 1121 days.

This patent is subject to a terminal disclaimer.

(21) Appl. No.: 17/555,658

(22) Filed: Dec. 20, 2021

(65) Prior Publication Data

US 2022/0110909 A1 Apr. 14, 2022

Related U.S. Application Data

(63) Continuation of application No. PCT/CN2019/091964, filed on Jun. 19, 2019.

(51) Int. Cl.

| | |
|---|---|
| ***A61K 31/337*** | (2006.01) |
| ***A61K 9/107*** | (2006.01) |
| ***A61K 47/10*** | (2017.01) |
| ***A61K 47/22*** | (2006.01) |
| ***A61K 47/24*** | (2006.01) |
| ***A61K 47/26*** | (2006.01) |
| ***A61K 47/28*** | (2006.01) |
| *A61K 47/02* | (2006.01) |
| *A61K 47/14* | (2017.01) |
| *A61K 47/44* | (2017.01) |
| *A61P 35/00* | (2006.01) |
| *C07C 271/22* | (2006.01) |
| *C07J 41/00* | (2006.01) |

(52) U.S. Cl.

CPC ............ *A61K 31/337* (2013.01); *A61K 9/107* (2013.01); *A61K 47/10* (2013.01); *A61K 47/22* (2013.01); *A61K 47/24* (2013.01); *A61K 47/26* (2013.01); *A61K 47/28* (2013.01)

(58) Field of Classification Search

CPC .. C07C 271/22; C07J 41/0061; C07J 41/0088

See application file for complete search history.

(56) References Cited

U.S. PATENT DOCUMENTS

| | | | |
|---|---|---|---|
| 10,172,795 | B2 | 1/2019 | Gao et al. |
| 2018/0244713 | A1 | 8/2018 | Li et al. |
| 2022/0110909 | A1 | 4/2022 | Gao |
| 2022/0356146 | A1 | 11/2022 | Engert et al. |

FOREIGN PATENT DOCUMENTS

| | | | |
|---|---|---|---|
| CN | 108026138 | A | 5/2018 |
| CN | 108310390 | A | 7/2018 |
| WO | 9629070 | A1 | 9/1996 |
| WO | 2017035501 | A1 | 3/2017 |

OTHER PUBLICATIONS

Dorwald F. A. Side Reactions in Organic Synthesis, 2005, Wiley: VCH, Weinheim pg. IX of Preface (Year: 2005).*

International Search Report of PCT Patent Application No. PCT/CN2019/091964 issued on Mar. 18, 2020.

Jun Wang et al., Synthesis of N Fmoc protection dipeptide of 11-deoxygly-cyrrhetinic acid derivatives, Chemical Reagents, Dec. 31, 2012, pp. 473-475, vol. 34, No. 5.

Jinghan Wang et al., Total Syntheses and Biological Activities of Vinylamycin Analogs, Journal of Medicinal Chemistry, Jan. 11, 2017, pp. 1189-1209, vol. 60, No. 3.

Extended European Search Report of European Patent Application No. 19934083.7 issued on Feb. 3, 2023.

K. H. Chang et al., Lithocholic acid analogues, new and potent α-2, 3-sialyltransferase inhibitors, Chem. Commun., Jan. 9, 2006, pp. 629-631.

D. B. Head et al., Use of the excluded protecting group (EPG) method for peptide synthesis, J. Peptide Res., Jan. 16, 2005, pp. 384-394, vol. 65.

Non-Final Office Action of U.S. Appl. No. 17/555,585 issued on Jul. 29, 2025.

Non-Final Office Action of U.S. Appl. No. 17/555,614 issued on Aug. 26, 2025.

Colin W. Pouton et al., Formulation of lipid-based delivery systems for oral administration: Materials, methods and strategies, Advanced Drug Delivery Reviews, 2008, pp. 625-637, vol. 60.

Ketan Hippalgaonkar et al., Injectable Lipid Emulsions-Advancements, Opportunities and Challenges, AAPS PharmSciTech, Dec. 4, 2010, pp. 1526-1540, vol. 11, No. 4.

Omar F. Luna et al., Deprotection Reagents in Fmoc Solid Phase Peptide Synthesis: Moving Away from Piperidine? Molecules, 2016, pp. 1-12, vol. 21, No. 1542.

* cited by examiner

*Primary Examiner* — Bruck Kifle
*Assistant Examiner* — Kevin S Martin

(57) ABSTRACT

The present invention relates to a method for preparing a modified hydrophobic excipient including the following steps: Step A. obtaining intermediate I or II from a hydrophobic natural compound with one to three hydroxyl groups or a hydrophobic synthetic compound with one to three hydroxyl groups and amino acid derivatives with amino protecting groups and different chain lengths acting as raw material; Step B. obtain intermediate III from an amino acid derivative and N-hydroxysuccinimide or 1-hydroxybenzotriazole acting as raw material and a dehydrating agent; and Step C. reacting the intermediate II and the intermediate III as raw material with an acid-binding agent under a dark condition to generate a modified hydrophobic excipient.

8 Claims, No Drawings

PREPARATION METHOD AND USE OF MODIFIED HYDROPHOBIC EXCIPIENT

CROSS-REFERENCE TO RELATED APPLICATION

This application is a continuation of international PCT application serial no. PCT/CN2019/091964, filed on Jun. 19, 2019. The entirety of the above-mentioned patent application is hereby incorporated by reference herein and made a part of this specification.

TECHNICAL FIELD

The present application relates to the application field of preparation of pharmaceutical excipient and drug-loaded fat emulsion, in particular to a modified hydrophobic excipient, preparation method and use thereof.

BACKGROUND ART

Many poorly water-soluble drugs require chemical or physical methods to increase water solubility and have to be prepared as injections before use. Drugs can be solubilized by chemical coupling with hydrophilic or amphiphilic excipients, or by preparation processes such as forming a molecular inclusion with cyclodextrin, forming a micelle, nano-dispersion and liposome with a surfactant, forming emulsion with a surfactant and an oil phase, and albumin wrapping.

Emulsion is a commonly used drug carrier to increase the solubility of poorly water-soluble drugs, while protecting the drugs from rapid degradation and altering the residence time of drugs in the blood and tissue distribution of drugs in the body. An emulsion is a dispersion of a liquid oil phase stabilized by a layer of hydrophilic surfactant in an aqueous phase. Solid Lipid Nanoparticles particularly refer to a dispersion of an oil phase stabilized by a layer of hydrophilic surfactant and assuming a solid state at normal temperature in an aqueous phase. A drug-loaded emulsion usually uses natural or synthetic triglyceride, fatty acid ester, cholesterol oleate or medium- and long-chain hydrocarbon as an oil phase, which have strong hydrophobicity. A drug has to be firstly well dissolved in a liquid oil phase before it can be prepared into a drug loaded emulsion is prepared. Therefore, the solubility of the drug in the oil phase is a key parameter for determining the drug loading capacity of the emulsion and the stability of the emulsion. However, many drugs have limited solubility in an oil phase having a strong hydrophobicity. Therefore, there will be very important practical significance to improve the solubility of hydrophobic drugs in an oil phase.

SUMMARY

In view of the defects present in existing technologies, a first purpose of the present application is to provide a modified hydrophobic excipient which has advantages of improving solubility of a drug in the hydrophobic excipient and increasing the drug loading capacity of the hydrophobic excipient.

In order to achieve the above purpose, the present application provides the following technical solutions:

In a first aspect, a modified hydrophobic excipient is provided, having the following molecular formula:

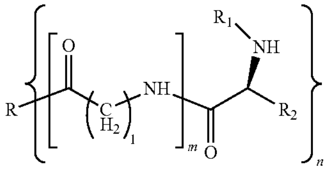

, where R is a hydrophobic natural compound or hydrophobic synthetic compound with one to three hydroxyl groups (n=1-3); R1 is an α-amino protecting group, and R2 is an amino acid side chain, wherein, when m=0, R reacts with an amino acid derivative with a protecting group by esterification to form a hydrophobic excipient carrying the amino acid derivative with a protecting group; or when m=1, R is first introduced with an amino acid linking arm of different chain lengths (1=1, 2, 4, 6) via an ester group, and then introduced with an amino acid derivative with a protecting group.

In a further development of the first aspect of the present application, the hydrophobic natural compound or hydrophobic synthetic compound with one to three hydroxyl groups (n=1-3) includes a triglyceride with one to three hydroxyl groups or a derivative thereof or a hydrophobic derivative of a steroid, or is obtained by introducing a hydroxyl group into an unsaturated triglyceride through an epoxy reaction and an electrophilic reaction or by introducing a hydroxyl group into an unsaturated triglyceride through a Michael reaction under a photocatalytic condition.

In a further development of the first aspect of the present application, the natural triglyceride with one to three hydroxyl groups is castor oil, and the derivative of the natural triglyceride with one to three hydroxyl groups is a hydrogenated derivative of castor oil.

In a further development of the first aspect of the present application, the hydrophobic derivative of the steroid is any one selected from a group consisting of an ester derivative or an amide derivative of cholic acid, an ester derivative or an amide derivative of deoxycholic acid, an ester derivative or an amide derivative of lithocholic acid, and an ester derivative or an amide derivative of glycocholic acid.

In a further development of the first aspect of the present application, the derivatives of the amino acids are any one selected from a group consisting of N-fluorenylmethoxycarbonyl-N'-tert-butoxycarbonyl-L-lysine, N-fluorenylmethoxycarbonyl-N'-tert-butoxycarbonyl-D-lysine, N-benzyloxycarbonyl-N'-tert-butoxycarbonyl-L-lysine, N-benzyloxycarbonyl-N'-tert-butoxycarbonyl-D-lysine, N-fluorenylmethoxycarbonyl-N'-benzyloxycarbonyl-L-lysine, N-fluorenylmethoxycarbonyl-N'-benzyloxycarbonyl-D-lysine, N-fluorenylmethoxycarbonyl-N'-fluorenylmethoxycarbonyl-L-lysine, N-fluorenylmethoxycarbonyl-N'-fluorenylmethoxycarbonyl-D-lysine, N-benzyloxycarbonyl-N'-benzyloxycarbonyl-L-lysine, N-benzyloxycarbonyl-N'-benzyloxycarbonyl-D-lysine, N-benzyloxycarbonyl-N'-fluorenylmethoxycarbonyl-L-lysine, N-benzyloxycarbonyl-N'-fluorenylmethoxycarbonyl-D-lysine, N-tert-butoxycarbonyl-N'-tert-butoxycarbonyl-L-lysine, N-tert-butoxycarbonyl-N'-tert-butoxycarbonyl-D-lysine, N-tert-butoxycarbonyl-N'-fluorenylmethoxycarbonyl-L-lysine, N-tert-butoxycarbonyl-N'-fluorenylmethoxycarbonyl-D-lysine, N-tert-butoxycarbonyl-N'-benzyloxycarbonyl-L-lysine, N-tert-butoxycarbonyl-N'-benzyloxycarbonyl-D-lysine, N-fluorenylmethoxycarbonyl-N'-tert-butoxycarbonyl-L-ornithine, N-fluorenylmethoxycarbonyl-N'-tert-butoxycarbonyl-D-ornithine, N-benzyloxycarbonyl-N'-tert-butoxycarbonyl-L-ornithine, N-benzyloxycarbonyl-N'-tert-butoxycarbonyl-D-ornithine, N-fluorenylmethoxycarbonyl-N'-fluorenylmethoxycarbonyl-L-ornithine, N-fluorenylmethoxycarbonyl-N'-benzyloxycarbonyl-L-ornithine, N-fluorenylmethoxycarbonyl-N'-benzyloxycarbonyl-D-ornithine, N-fluorenylmethoxycarbonyl-N'-fluorenylmethoxycarbonyl-L-ornithine, N-fluorenylmethoxycarbonyl-N'-fluorenylmethoxycarbonyl-D-ornithine, N-benzyloxycarbonyl-N'-benzyloxycarbonyl-L-ornithine, N-benzyloxycarbonyl-N'-benzyloxycarbonyl-D-ornithine, N-benzyloxycarbonyl-N'-fluorenylmethoxycarbonyl-L-ornithine, N-benzyloxycarbonyl-N'-fluorenylmethoxycarbonyl-D-ornithine, N-tert-butoxycarbonyl-N'-tert-butoxycarbonyl-L-ornithine, N-tert-butoxycarbonyl-N'-tert-butoxycarbonyl-D-ornithine, N-tert-butoxycarbonyl-N'-fluorenylmethoxycarbonyl-L-ornithine, N-tert-butoxycarbonyl-N'-fluorenylmethoxycarbonyl-D-ornithine, N-tert-butoxycarbonyl-N'-benzyloxycarbonyl-L-ornithine, N-tert-butoxycarbonyl-N'-benzyloxycarbonyl-D-ornithine, N-fluorenylmethoxycarbonyl-N'-tert-butoxycarbonyl-L-tryptophan, N-fluorenylmethoxycarbonyl-N'-tert-butoxycarbonyl-D-tryptophan, N-benzyloxycarbonyl-N'-tert-butoxycarbonyl-L-tryptophan, N-benzyloxycarbonyl-N'-tert-butoxycarbonyl-D-tryptophan, N-fluorenylmethoxycarbonyl-N'-benzyloxycarbonyl-L-tryptophan, N-fluorenylmethoxycarbonyl-N'-benzyloxycarbonyl-D-tryptophan, N-fluorenylmethoxycarbonyl-N'-fluorenylmethoxycarbonyl-L-tryptophan, N-fluorenylmethoxycarbonyl-N'-fluorenylmethoxycarbonyl-D-tryptophan, N-benzyloxycarbonyl-N'-benzyloxycarbonyl-L-tryptophan, N-benzyloxycarbonyl-N'-benzyloxycarbonyl-D-tryptophan, N-tert-butoxycarbonyl-N'-tert-butoxycarbonyl-L-tryptophan, N-tert-butoxycarbonyl-N'-tert-butoxycarbonyl-D-tryptophan, N-fluorenylmethoxycarbonyl-O'-benzyl ester-L-aspartic acid, N-fluorenylmethoxycarbonyl-O'-benzyl ester-D-aspartic acid, N-benzyloxycarbonyl-O'-benzyl ester-L-aspartic acid, N-benzyloxycarbonyl-O'-benzyl ester-D-aspartic acid, N-tert-butoxycarbonyl-O'-benzyl ester-L-aspartic acid, N-tert-butoxycarbonyl-O'-benzyl ester-D-aspartic acid, N-tert-butoxycarbonyl-O-benzyl ester-L-aspartic acid, N-tert-butoxycarbonyl-O-benzyl ester-D-aspartic acid, N-fluorenylmethoxycarbonyl-O'-methyl ester-L-aspartic acid, N-fluorenylmethoxycarbonyl-O'-methyl ester-D-aspartic acid, N-benzyloxycarbonyl-O'-methyl ester-L-aspartic acid, N-benzyloxycarbonyl-O'-methyl ester-D-aspartic acid, N-tert-butoxycarbonyl-O'-methyl ester-L-aspartic acid, N-tert-butoxycarbonyl-O'-methyl ester-D-aspartic acid, N-tert-butoxycarbonyl-O-methyl ester-L-aspartic acid, N-tert-butoxycarbonyl-O-methyl ester-D-aspartic acid, N-fluorenylmethoxycarbonyl-O'-ethyl ester-L-aspartic acid, N-fluorenylmethoxycarbonyl-O'-ethyl ester-D-aspartic acid, N-benzyloxycarbonyl-O'-ethyl ester-L-aspartic acid, N-benzyloxycarbonyl-O'-ethyl ester-D-aspartic acid, N-tert-butoxycarbonyl-O'-ethyl ester-L-aspartic acid, N-tert-butoxycarbonyl-O'-ethyl ester-D-aspartic acid, N-tert-butoxycarbonyl-O-ethyl ester-L-aspartic acid, N-tert-butoxycarbonyl-O-ethyl ester-D-aspartic acid, N-fluorenylmethoxycarbonyl-O'-tert-butyl ester-L-aspartic acid, N-fluorenylmethoxycarbonyl-O'-tert-butyl ester-D-aspartic acid, N-benzyloxycarbonyl-O'-tert-butyl ester-L-aspartic acid, N-benzyloxycarbonyl-O'-tert-butyl ester-D-aspartic acid, N-tert-butoxycarbonyl-O'-tert-butyl ester-L-aspartic acid, N-tert-butoxycarbonyl-O'-tert-butyl ester-D-aspartic acid, N-tert-butoxycarbonyl-O-tert-butyl ester-L-aspartic acid, N-tert-butoxycarbonyl-O-tert-butyl ester-D-aspartic acid, N-fluorenylmethoxycarbonyl-O'-allyl ester-L-aspartic acid, N-fluorenylmethoxycarbonyl-O'-allyl ester-D-aspartic acid, N-benzyloxycarbonyl-O'-allyl ester-L-aspartic acid, N-benzyloxycarbonyl-O'-allyl ester-D-aspartic acid, N-tert-butoxycarbonyl-O'-allyl ester-L-aspartic acid, N-tert-butoxycarbonyl-O'-allyl ester-D-aspartic acid, N-tert-butoxycarbonyl-O-allyl ester-L-aspartic acid, N-tert-butoxycarbonyl-O-allyl ester-D-aspartic acid, N-fluorenylmethoxycarbonyl-O'-benzyl ester-L-glutamic acid, N-fluorenylmethoxycarbonyl-O'-benzyl ester-D-glutamic acid, N-benzyloxycarbonyl-O'-benzyl ester-L-glutamic acid, N-benzyloxycarbonyl-O'-benzyl ester-D-glutamic acid, N-tert-butoxycarbonyl-O'-benzyl ester-L-glutamic acid, N-tert-butoxycarbonyl-O'-benzyl ester-D-glutamic acid, N-tert-butoxycarbonyl-O-benzyl ester-L-glutamic acid, N-tert-butoxycarbonyl-O-benzyl ester-D-glutamic acid, N-fluorenylmethoxycarbonyl-O'-methyl ester-L-glutamic acid, N-fluorenylmethoxycarbonyl-O'-methyl ester-D-glutamic acid, N-benzyloxycarbonyl-O'-methyl ester-L-glutamic acid, N-benzyloxycarbonyl-O'-methyl ester-D-glutamic acid, N-tert-butoxycarbonyl-O'-methyl ester-L-glutamic acid, N-tert-butoxycarbonyl-O'-methyl ester-D-glutamic acid, N-tert-butoxycarbonyl-O-methyl ester-L-glutamic acid, N-tert-butoxycarbonyl-O-methyl ester-D-glutamic acid, N-fluorenylmethoxycarbonyl-O'-ethyl ester-L-glutamic acid, N-fluorenylmethoxycarbonyl-O'-ethyl ester-D-glutamic acid, N-benzyloxycarbonyl-O'-ethyl ester-L-glutamic acid, N-benzyloxycarbonyl-O'-ethyl ester-D-glutamic acid, N-tert-butoxycarbonyl-O'-ethyl ester-L-glutamic acid, N-tert-butoxycarbonyl-O'-ethyl ester-D-glutamic acid, N-tert-butoxycarbonyl-O-ethyl ester-L-glutamic acid, N-tert-butoxycarbonyl-O-ethyl ester-D-glutamic acid, N-fluorenylmethoxycarbonyl-O'-tert-butyl ester-L-glutamic acid, N-fluorenylmethoxycarbonyl-O'-tert-butyl ester-D-glutamic acid, N-benzyloxycarbonyl-O'-tert-butyl ester-L-glutamic acid, N-benzyloxycarbonyl-O'-tert-butyl ester-D-glutamic acid, N-tert-butoxycarbonyl-O'-tert-butyl ester-L-glutamic acid, N-tert-butoxycarbonyl-O'-tert-butyl ester-D-glutamic acid, N-tert-butoxycarbonyl-O-tert-butyl ester-L-glutamic acid, N-tert-butoxycarbonyl-O-tert-butyl ester-D-glutamic acid, N-fluorenylmethoxycarbonyl-O'-allyl ester-L-glutamic acid, N-fluorenylmethoxycarbonyl-O'-allyl ester-D-glutamic acid, N-benzyloxycarbonyl-O'-allyl ester-L-glutamic acid, N-benzyloxycarbonyl-O'-allyl ester-D-glutamic acid, N-tert-butoxycarbonyl-O'-allyl ester-L-glutamic acid, N-tert-butoxycarbonyl-O'-allyl ester-D-glutamic acid, N-tert-butoxycarbonyl-O-allyl ester-L-glutamic acid, N-tert-butoxycarbonyl-O-allyl ester-D-glutamic acid, N-fluorenylmethoxycarbonyl-L-asparagine, N-fluorenylmethoxycarbonyl-D-asparagine, N-benzyloxycarbonyl-L-asparagine, N-benzyloxycarbonyl-D-asparagine, N-tert-butoxycarbonyl-L-asparagine, N-tert-butoxycarbonyl-D-asparagine, N-fluorenylmethoxycarbonyl-L-glutamine, N-fluorenylmethoxycarbonyl-D-glutamine, N-benzyloxycarbonyl-L-glutamine, N-benzyloxycarbonyl-D-glutamine, N-tert-butoxycarbonyl-L-glutamine, N-tert-butoxycarbonyl-D-glutamine, N-fluorenylmethoxycarbonyl-O-acetyl-L-serine, N-fluorenylmethoxycarbonyl-O-acetyl-D-serine, N-benzyloxycarbonyl-O-acetyl-L-serine, N-benzyloxycarbonyl-O-acetyl-D-serine, N-tert-butoxycarbonyl-O-acetyl-L-serine, N-tert-butoxycarbonyl-O-acetyl-D-serine, N-fluorenylmethoxycarbonyl-O-benzyl-L-serine, N-fluorenylmethoxycarbonyl-O-benzyl-D-serine, N-benzyloxycarbonyl-O-benzyl-L-serine, N-benzyloxycarbonyl-O-benzyl-D-serine, N-tert-butoxycarbonyl-O-benzyl-L-serine, N-tert-butoxycarbonyl-O-benzyl-D-serine, N-fluorenylmethoxycarbonyl-O-tert-butyl-L-serine, N-fluorenylmethoxycarbonyl-O-tert-butyl-D-serine, N-benzyloxycarbonyl-O-tert-butyl-L-serine, N-benzyloxycarbonyl-O-tert-butyl-D-serine, N-tert-butoxycarbonyl-O-tert-butyl-L-serine, N-tert-butoxycarbonyl-O-tert-butyl-D-serine, N-fluorenylmethoxycarbonyl-O-allyl-L-serine, N-fluorenylmethoxycarbonyl-O-allyl-D-serine, N-benzyloxycarbonyl-O-allyl-L-serine, N-benzyloxycarbonyl-O-allyl-D-serine, N-tert-butoxycarbonyl-O-allyl-L-serine; N-tert-butoxycarbonyl-O-allyl-D-serine; N-fluorenylmethoxycarbonyl-O-acetyl-L-threonine, N-fluorenylmethoxycarbonyl-O-acetyl-D-threonine, N-benzyloxycarbonyl-O-acetyl-L-threonine, N-benzyloxycarbonyl-O-acetyl-D-threonine, N-tert-butoxycarbonyl-O-acetyl-L-threonine, N-tert-butoxycarbonyl-O-acetyl-D-threonine, N-fluorenylmethoxycarbonyl-O-benzyl-L-threonine, N-fluorenylmethoxycarbonyl-O-benzyl-D-threonine, N-benzyloxycarbonyl-O-benzyl-L-threonine, N-benzyloxycarbonyl-O-benzyl-D-threonine, N-tert-butoxycarbonyl-O-benzyl-L-threonine, N-tert-butoxycarbonyl-O-benzyl-D-threonine, N-fluorenylmethoxycarbonyl-O-tert-butyl-L-threonine, N-fluorenylmethoxycarbonyl-O-tert-butyl-D-threonine, N-benzyloxycarbonyl-O-tert-butyl-L-threonine, N-benzyloxycarbonyl-O-tert-butyl-D-threonine, N-tert-butoxycarbonyl-O-tert-butyl-L-threonine, N-tert-butoxycarbonyl-O-tert-butyl-D-threonine, N-fluorenylmethoxycarbonyl-O-allyl-L-threonine, N-fluorenylmethoxycarbonyl-O-allyl-D-threonine, N-benzyloxycarbonyl-O-allyl-L-threonine, N-benzyloxycarbonyl-O-allyl-D-threonine, N-tert-butoxycarbonyl-O-allyl-L-threonine, N-tert-butoxycarbonyl-O-allyl-D-threonine, N-fluorenylmethoxycarbonyl-NG-2,2,4,6,7-pentamethylbenzofuran-5-sulfonyl-L-arginine, N-fluorenylmethoxycarbonyl-NG-2,2,4,6,7-pentamethylbenzofuran-5-sulfonyl-D-arginine, N-benzyloxycarbonyl-NG-2,2,4,6,7-pentamethylbenzofuran-5-sulfonyl-L-arginine, N-benzyloxycarbonyl-NG-2,2,4,6,7-pentamethylbenzofuran-5-sulfonyl-D-arginine, N-tert-butoxycarbonyl-NG-2,2,4,6,7-pentamethylbenzofuran-5-sulfonyl-L-arginine, N-tert-butoxycarbonyl-NG-2,2,4,6,7-pentamethylbenzofuran-5-sulfonyl-D-arginine, N-fluorenylmethoxycarbonyl-N'-(4-methoxy-2,3,6-trimethylbenzenesulfonyl)-L-arginine, N-fluorenylmethoxycarbonyl-N'-(4-methoxy-2,3,6-trimethylbenzenesulfonyl)-D-arginine, N-benzyloxycarbonyl-N'-(4-methoxy-2,3,6-trimethylbenzenesulfonyl)-L-arginine, N-benzyloxyca- rbonyl-N'-(4-methoxy-2,3,6-trimethylbenzenesulfonyl)-D-arginine, N-tert-butoxycarbonyl-N'-(4-methoxy-2,3,6-trimethylbenzenesulfonyl)-L-arginine, N-tert-butoxycarbonyl-N'-(4-methoxy-2,3,6-trimethylbenzenesulfonyl)-D-arginine, N-fluorenylmethoxycarbonyl-glycine, N-benzyloxycarbonyl-glycine, N-tert-butoxycarbonyl-glycine, N-fluorenylmethoxycarbonyl-β-alanine, N-benzyloxycarbonyl-β-alanine, N-tert-butoxycarbonyl-β-alanine, N-fluorenylmethoxycarbonyl-L-valine, N-fluorenylmethoxycarbonyl-D-valine, N-benzyloxycarbonyl-L-valine, N-benzyloxycarbonyl-D-valine, N-tert-butoxycarbonyl-L-valine, N-tert-butoxycarbonyl-D-valine, N-tert-butyloxycarbonyl-L-alanine, N-fluoromethoxycarbonyl-D-alanine, N-benzyloxycarbonyl-L-alanine, N-benzyloxycarbonyl-D-alanine, N-tert-butoxycarbonyl-L-alanine, N-tert-butoxycarbonyl-D-alanine, N-fluorenylmethoxycarbonyl-L-leucine, N-fluorenylmethoxycarbonyl-D-leucine, N-benzyloxycarbonyl-L-leucine, N-benzyloxycarbonyl-D-leucine, N-tert-butoxycarbonyl-L-leucine, N-tert-butoxycarbonyl-D-leucine, N-fluorenylmethoxycarbonyl-L-isoleucine, N-fluorenylmethoxycarbonyl-D-isoleucine, N-benzyloxycarbonyl-L-isoleucine, N-benzyloxycarbonyl-D-isoleucine, N-tert-butoxycarbonyl-L-isoleucine, N-tert-butoxycarbonyl-D-isoleucine, N-fluorenylmethoxycarbonyl-L-methionine, N-fluorenylmethoxycarbonyl-D-methionine, N-benzyloxycarbonyl-L-methionine, N-benzyloxycarbonyl-D-methionine, N-tert-butoxycarbonyl-L-methionine, N-tert-butoxycarbonyl-D-methionine, N-fluorenylmethoxycarbonyl-L-tyrosine, N-fluorenylmethoxycarbonyl-D-tyrosine, N-benzyloxycarbonyl-L-tyrosine, N-benzyloxycarbonyl-D-tyrosine, N-tert-butoxycarbonyl-L-tyrosine, N-tert-butoxycarbonyl-D-tyrosine, N-fluorenylmethoxycarbonyl-L-acetyltyrosine, N-fluorenylmethoxycarbonyl-D-acetyltyrosine, N-benzyloxycarbonyl-L-acetyltyrosine, N-benzyloxycarbonyl-D-acetyltyrosine, N-tert-butoxycarbonyl-L-acetyltyrosine, N-tert-butoxycarbonyl-D-acetyltyrosine, N-fluorenylmethoxycarbonyl-L-phenylalanine, N-fluorenylmethoxycarbonyl-D-phenylalanine, N-benzyloxycarbonyl-L-phenylalanine, N-benzyloxycarbonyl-D-phenylalanine, N-tert-butoxycarbonyl-L-phenylalanine, and N-tert-butoxycarbonyl-D-phenylalanine.

In a further development of the first aspect of the present application, the amino protecting group is any one selected from a group consisting of fluorenylmethoxycarbonyl (Fmoc group), benzyloxycarbonyl (Cbz group), tert-butyloxycarbonyl (Boc group), benzoyl, formyl, acetyl or trifluoroacetyl group.

In a further development of the first aspect of the present application, the amino acid derivative is a glycine derivative or a lysine derivative.

In a further development of the first aspect of the present application, the glycine derivative is selected from a group consisting of N-fluorenylmethoxycarbonyl-glycine, N-benzyloxycarbonyl-glycine and N-tert-butoxycarbonyl-glycine, and the lysine derivative is selected from a group consisting of N-fluorenylmethoxycarbonyl-N'-tert-butoxycarbonyl-L-lysine, N-fluorenylmethoxycarbonyl-N'-tert-butoxycarbonyl-D-lysine, N-benzyloxycarbonyl-N'-tert-butoxycarbonyl-L-lysine, N-benzyloxycarbonyl-N'-tert-butoxycarbonyl-D-lysine, N-fluorenylmethoxycarbonyl-N'-benzyloxycarbonyl-L-lysine, N-fluorenylmethoxycarbonyl-N'-benzyloxycarbonyl-D-lysine, N-fluorenylmethoxycarbonyl-N'-fluorenylmethoxycarbonyl-L-lysine, N-fluorenylmethoxycarbonyl-N'-fluorenylmethoxycarbonyl-D-lysine, N-benzyloxycarbonyl-N'-benzyloxycarbonyl-L-lysine, N-benzyloxycarbonyl-N'-benzyloxycarbonyl-D-lysine, N-benzyloxycarbonyl-N'-fluorenylmethoxycarbonyl-L-lysine, N-benzyloxycarbonyl-N'-fluorenylmethoxycarbonyl-D-lysine, N-tert-butoxycarbonyl-N'-tert-butoxycarbonyl-L-lysine, N-tert-butoxycarbonyl-N'-tert-butoxycarbonyl-D-lysine, N-tert-butoxycarbonyl-N'-fluorenylmethoxycarbonyl-L-lysine, N-tert-butoxycarbonyl-N'-fluorenylmethoxycarbonyl-D-lysine, N-tert-butoxycarbonyl-N'-benzyloxycarbonyl-L-lysine, and N-tert-butoxycarbonyl-N'-benzyloxycarbonyl-D-lysine.

In a second aspect, the present application provides a hydrophobic excipient having the following formula:

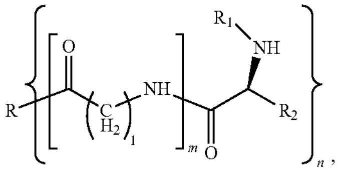

where R is a triglyceride with one to three hydroxyl groups (n=1-3) or a derivative of the triglyceride with one to three hydroxyl groups or a hydrophobic derivative of a steroid, R1 is any one selected from a group consisting of fluorenylmethoxycarbonyl (Fmoc group) or benzyloxycarbonyl (Cbz group) or tert-butoxycarbonyl (Boc group) or benzoyl or formyl or acetyl or trifluoroacetyl group, and R2 is an amino acid side chain; wherein, when m=0, R is reacted with an amino acid derivative with fluorenylmethoxycarbonyl (Fmoc group) or benzyloxycarbonyl (Cbz group) or tert-butyloxycarbonyl (Boc group) or benzoyl or formyl or acetyl or trifluoroacetyl protecting group through esterification to form the hydrophobic excipient; or when m=1, R is firstly introduced with an amino acid linking arm of different chain lengths (l=1, 2, 4, 6) via an ester group, and then introduced with a glycine derivative or a lysine derivative with a protecting group such as fluorenylmethoxycarbonyl (Fmoc group), benzyloxycarbonyl (Cbz group), tert-butyloxycarbonyl (Boc group), benzoyl, formyl, acetyl or trifluoroacetyl group to form the hydrophobic excipient.

In a further development of the second aspect of the present application, the natural triglyceride with one to three hydroxyl groups include castor oil; and the derivatives of natural triglycerides with one to three hydroxyl group includes hydrogenated derivatives of castor oil.

In a further development of the second aspect of the present application, the hydrophobic derivative of the steroid is selected from a group consisting of ester derivatives or amide derivatives of cholic acid, ester derivatives or amide derivatives of deoxycholic acid, ester derivatives or amide derivatives of lithocholic acid, and ester derivatives or amide derivatives of glycocholic acid.

In a further development of the second aspect of the present application, the amide derivative of cholic acid is cholic acid-N-oleylamine.

In a further development of the second aspect of the present application, the glycine derivative is selected from a group consisting of N-fluorenylmethoxycarbonyl-glycine, N-benzyloxycarbonyl-glycine and N-tert-butoxycarbonyl-glycine; and the lysine derivative is selected from a group consisting of N-fluorenylmethoxycarbonyl-N'-tert-butoxycarbonyl-L-lysine, N-fluorenylmethoxycarbonyl-N'-tert-butoxycarbonyl-D-lysine, N-benzyloxycarbonyl-N'-tert-butoxycarbonyl-L-lysine, N-benzyloxycarbonyl-N'-tert-butoxycarbonyl-D-lysine, N-fluorenylmethoxycarbonyl-N'-benzyloxycarbonyl-L-lysine, N-fluorenylmethoxycarbonyl-N'-benzyloxycarbonyl-D-lysine, N-fluorenylmethoxycarbonyl-N'-fluorenylmethoxycarbonyl-L-lysine, N-fluorenylmethoxycarbonyl-N'-fluorenylmethoxycarbonyl-D-lysine, N-benzyloxycarbonyl-N'-benzyloxycarbonyl-L-lysine, N-benzyloxycarbonyl-N'-benzyloxycarbonyl-D-lysine, N-benzyloxycarbonyl-N'-fluorenylmethoxycarbonyl-L-lysine, N-benzyloxycarbonyl-N'-fluorenylmethoxycarbonyl-D-lysine, N-tert-butoxycarbonyl-N'-tert-butoxycarbonyl-L-lysine, N-tert-butoxycarbonyl-N'-tert-butoxycarbonyl-D-lysine, N-tert-butoxycarbonyl-N'-fluorenylmethoxycarbonyl-L-lysine, N-tert-butoxycarbonyl-N'-fluorenylmethoxycarbonyl-D-lysine, N-tert-butoxycarbonyl-N'-benzyloxycarbonyl-L-lysine, and N-tert-butoxycarbonyl-N'-benzyloxycarbonyl-D-lysine.

In a further development of the second aspect of the present application, the glycine derivative is selected from a group consisting of N-fluorenylmethoxycarbonyl-glycine, N-benzyloxycarbonyl-glycine and N-tert-butoxycarbonyl-glycine, and the lysine derivative is N-fluorenylmethoxycarbonyl-N'-tert-butoxycarbonyl-L-lysine.

The technical solution is designed based on the principle as follows. The conventional hydrophobic excipients mainly dissolve and load a hydrophobic drug in a hydrophobic excipient through hydrophobic effect. However, since the solubility of the hydrophobic drug in the hydrophobic excipient with extremely strong hydrophobicity is limited, the hydrophobic drug tends to be crystallized and separated out when exceeding the solubility of the hydrophobic drug. In view of the fact that a plurality of hydrophobic drugs have aromatic benzene rings or derivatives thereof or heterocycles in the structure, introducing an amino acid with aromatic rings into hydrophobic excipients with one or more hydroxyl groups will provide the modified hydrophobic excipients with a function, which is beneficial for the stacking of aromatic groups between the modified hydrophobic excipients and drugs containing aromatic groups. Further, most of the hydrophobic drugs generally contain chemical bonds capable of forming hydrogen bonds, therefore, noncovalent physical interactions can occur between the carbamoyl groups and amide groups on the amino acid derivatives and the drugs via hydrogen bonds. Due to the two kinds of extra molecular reactions, the modified hydrophobic excipient is favorable for improving the compatibility with the hydrophobic drug, so that the solubility of the drug is favorably increased, the stability of the drug-loaded fat emulsion is favorably improved, and meanwhile, the application range of the drug loading of the modified hydrophobic excipient is wider. In order to overcome possible steric hindrance, an amino acid linking arm with different chain lengths can be introduced into the hydrophobic excipients with one or more hydroxyl groups through an ester group, and then the amino acid with aromatic rings is introduced into the amino acid linking arm.

In view of the defects present in existing technologies, a second purpose of the present application is to provide a preparation method of a modified hydrophobic excipient, and the prepared modified hydrophobic excipient has advantages of being beneficial to improve the solubility of the hydrophobic drug in the modified hydrophobic excipient.

In order to achieve the above purpose, the present application provides the following technical solutions.

In a third aspect, the present application provides a method for preparing the modified hydrophobic excipient according to the first aspect, wherein a hydrophobic natural compound with one to three hydroxyl groups or a hydrophobic synthetic compound with one to three hydroxyl groups and an amino acid derivative acting as raw material, a dehydrating agent and a catalyst are subjected to an esterification reaction according to the following reaction formula to obtain the modified hydrophobic excipient, where n is 1-3,

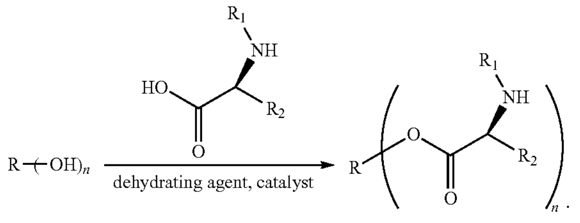

In the above technical solution, since the hydroxyl is a hydrophilic group, the carboxyl on the amino acid derivative is reacted with the hydroxyl on the hydrophobic natural compound with one to three hydroxyl groups or the hydrophobic synthetic compound with one to three hydroxyl groups to form an ester bond, which is beneficial to improve the hydrophobicity of the excipient. Further, the group containing an aromatic ring and the group containing carbamoyl or amide are introduced into the hydrophobic excipient, and are combined with the hydrophobic compounds through physical actions such as aromatic ring stacking, hydrogen bond and the like. Therefore, the compatibility of the hydrophobic excipient and the hydrophobic drug is favorably improved, the solubility of the drug is increased, and the stability of the drug-loaded fat emulsion is improved, so that the application range of the hydrophobic excipient is expanded.

In a further development of the third aspect of the present application, the dehydrating agent can be any one selected from a group consisting of dicyclohexylcarbodiimide, N,N'-diisopropyl carbodiimide, 1-(3-dimethylaminopropyl)-3-ethylcarbodiimide hydrochloride, diphenyl-phosphoryl azide, p-toluenesulfonyl azide, and the like.

In a further development of the third aspect of the present application, the catalyst can be any one selected from a group consisting of 4-dimethylpyridine, immobilized 4-dimethylpyridine and pyridine.

In a further development of the third aspect of the present application, the dehydrating agent is any one selected from a group consisting of dicyclohexylcarbodiimide (DCC), diisopropylcarbodiimide (DIC) and 1-(3-dimethylaminopropyl)-3-ethylcarbodiimide (EDC), and the catalyst is any one selected from a group consisting of 4-dimethylaminopyridine (DMAP) and immobilized DMAP.

In the above technical solution, the dicyclohexylcarbodiimide or diisopropyl-carbodiimide or 1-(3-dimethylaminopropyl)-3-ethylcarbodiimide as a dehydrating agent is cooperated with 4-dimethylaminopyridine or immobilized DMAP as a catalyst, so that the activity of the reaction is improved, and the reaction rate is accelerated.

In view of the defects present in existing technologies, the third purpose of the present application is to provide a preparation method of the modified hydrophobic excipient, which has the advantage that the prepared modified hydrophobic excipient is beneficial to improving the solubility of the hydrophobic drug in the hydrophobic excipient.

In order to achieve the above purpose, the present application provides the following technical solutions:

In a fourth aspect, the present application provides a method for preparing the modified hydrophobic excipient according to the second aspect, including the following steps: Step A. subjecting a hydrophobic natural compound with one to three hydroxyl groups or a hydrophobic synthetic compound with one to three hydroxyl groups and amino acid derivatives with N-tert-butyloxycarbonyl protecting group or N-benzyloxycarbonyl protecting group acting as raw materials, a dehydrating agent and a catalyst to an esterification reaction to generate intermediate I of amino acid derivatives with N-tert-butyloxycarbonyl protecting group or N-benzyloxycarbonyl protecting group, and adding an organic acid or an inorganic acid to the amino acid derivatives with N-tert-butyloxycarbonyl protecting group to remove the amino protecting group or catalytically hydrogenating the amino acid derivatives with N-benzyloxycarbonyl protecting group to remove the amino protecting group, so as to obtain intermediate II with amino groups, according to the following reaction formula, where R3 is an α-amino protecting group, n is 1-3, and 1=1, 2, 4, 6;

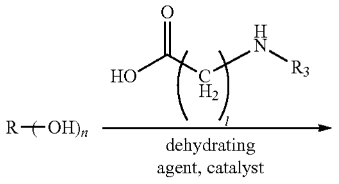

-continued

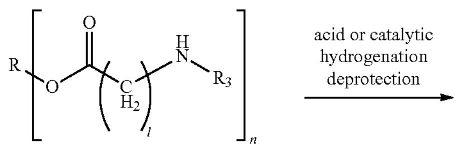

intermediate I

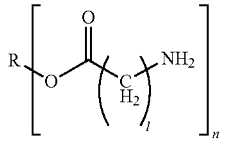

intermediate II

Step B. subjecting an amino acid derivative and N-hydroxysuccinimide or 1-hydroxybenzo-triazole acting as raw material and a dehydrating agent to an esterification reaction to obtain intermediate III, according to the following reaction formula, where R1 is an alpha-amino protecting group, and R2 is an amino acid side chain; and

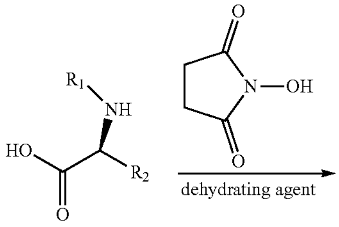

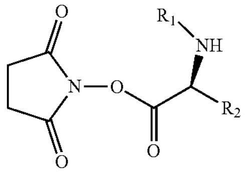

or

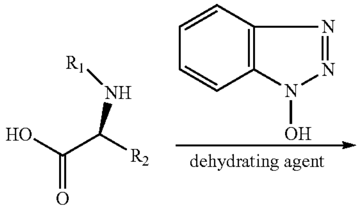

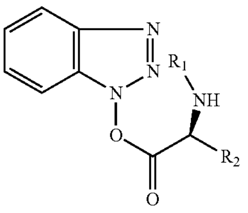

Step C. reacting the intermediate II and the intermediate III as raw materials with an acid-binding agent under a dark condition to obtain a modified hydrophobic excipient, according to the following reaction formula, where, n is 1-3, and 1 is 1, 2, 4 and 6.

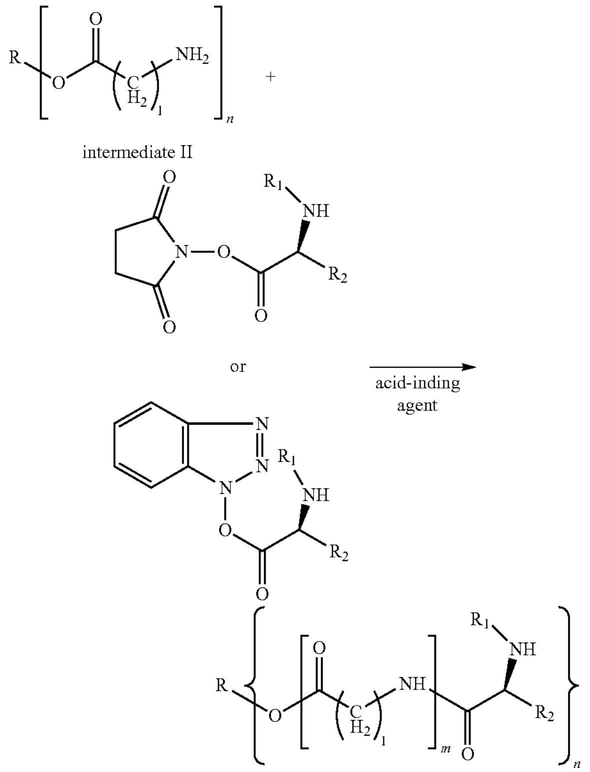

In the above technical solution, the hydroxyl on the hydrophobic excipient is modified by the protected amino acid, and then the amino protecting group is removed to form the intermediate II carrying an amino group. Thereby, a small intermolecular arm is introduced onto the hydrophobic excipient, which can the problem of incomplete coupling reaction due to steric hindrance. Carboxyl on the amino acid derivative is activated firstly by N-hydroxysuccinimide or 1-hydroxybenzotriazole to form N-hydroxysuccinimide or 1-hydroxybenzotriazole active ester (intermediate III) of the amino acid derivative, and thus can be easily bonded with amino on hydrophobic excipient amino acid ester. The reaction of the intermediate II and the intermediate III provides the generated hydrophobic excipient with both an aromatic ring substituent group and a carbamoyl group or an amide group. Therefore, the hydrophobic excipient can be favorably combined with a hydrophobic compound through the carried aromatic ring-containing group and the carried carbamoyl group or amide group through non-covalent physical actions such as aromatic ring stacking, hydrogen bond and the like. In turn, the compatibility of the hydrophobic excipient and a hydrophobic drug is favorably increased, the solubility of the drug is increased, and the stability of the drug-loaded fat emulsion is improved. Thus, the hydrophobic excipient can be combined with various hydrophobic drugs, and the application range of the hydrophobic excipient is favorably expanded.

In a further development of the fourth aspect of the present application, the dehydrating agent can be any one selected from a group consisting of dicyclohexylcarbodiimide, N, N'-diisopropylcarbodiimide, 1-(3-dimethylaminopropyl)-3-ethylcarbodiimide hydrochloride, diphenylphosphoryl azide, p-toluenesulfonyl azide, and the like.

In a further development of the fourth aspect of the present application, the catalyst can be any one selected from a group consisting of 4-dimethyl pyridine, immobilized 4-dimethyl pyridine, pyridine, and the like.

In a further development of the fourth aspect of the present application, the acid-binding agent can be any one selected from a group consisting of triethylamine, diisopropylamine, pyridine, and the like.

In a further development of the fourth aspect of the present application, the dehydrating agent is dicyclohexylcarbodiimide, and the catalyst is 4-dimethylaminopyridine.

In the above technical solution, dicyclohexylcarbodiimide as the dehydrating agent is cooperated with 4-dimethylaminopyridine as the catalyst, so that the activity of the reaction is improved, the reaction rate is accelerated, and the post-treatment of the reaction is facilitated.

In a further development of the fourth aspect of the present application, in Step A, the catalytic hydrogenation reaction condition is $H_2$ (1-5 atm) and Pt/C as catalyst.

In the above technical solution, the catalyst used for removing the N-benzyloxycarbonyl by catalytic hydrogenation is 5% palladium carbon (Pt/C), and the dosage of the catalyst is 1-10%. The hydrogen pressure is 1-5 atm, and the reaction time is 1-12 hours at room temperature. When N-benzyloxycarbonyl is removed by catalytic hydrogenation, a proper amount of acetic acid can be added for neutralizing newly generated amino groups and preventing the amino groups from participating in a side reaction and inhibiting the activity of the catalyst.

In a further development of the fourth aspect of the present application, in Step A, the amino protecting group is N-tert-butyloxycarbonyl or N-benzyloxycarbonyl, wherein the N-tert-butyloxycarbonyl and the N-benzyloxycarbonyl are removed by acid or catalytic hydrogenation respectively, and the intermediate I is dissolved in a solvent before adding the acid or performing hydrogenation.

In the above technical solution, dissolving the intermediate I in a solvent before adding the acid or performing hydrogen is beneficial to the complete dissolution of the intermediate I, such that the intermediate I can better react with the organic acid or the inorganic acid, and the conversion efficiency can be improved.

In a further development of the fourth aspect of the present application, the solvent can be any one selected from a group consisting of dichloromethane, ethyl acetate or tetrahydrofuran.

In a further development of the fourth aspect of the present application, the acid-binding agent is triethylamine.

In the above technical solution, by using the triethylamine as the acid-binding agent, the reaction activity of the intermediate II and the intermediate III is favorably improved, and the modified hydrophobic excipient is easier to generate.

In view of the defects present in existing technologies, a fourth purpose of the present application is to provide a use of the modified hydrophobic excipient as an oil phase excipient, which can increase the solubility of the hydrophobic drug in the modified hydrophobic excipient, and can be combined with a proper surfactant to improve the drug loading capacity and the stability of the drug-loaded fat emulsion.

In a fifth aspect, to achieve the above object, the present application provides a technical solution of a drug-loaded emulsion composed of the modified hydrophobic excipient according to the first or second aspect, a hydrophobic drug and a surfactant. The modified hydrophobic excipient, the hydrophobic drug and the surfactant are dissolved in a proper solvent, the solvent is removed, a buffer solution is added for hydration, and the drug-loaded fat emulsion can be prepared by a proper preparation method.

In a further development of the fifth aspect of the present application, the modified hydrophobic excipient is protected amino acid ester of the hydrophobic excipient or protected amino acid amide of the hydrophobic excipient amino acid ester.

In a further development of the fifth aspect of the present application, the hydrophobic drugs are paclitaxel, docetaxel and other hydrophobic drugs which may have intermolecular interaction with the modified hydrophobic excipients such as aromatic ring stacking, hydrogen bond or hydrophobic interaction.

In a further development of the fifth aspect of the present application, the ratio between the hydrophobic drug and the modified hydrophobic excipient may be any proper ratio, for example, 0.01% (w/w)-99.9% (w/w) to 99.9% (w/w)-0.01 (w/w), a preferred ratio between the hydrophobic drug and the modified hydrophobic excipient is 1% (w/w)-50% (w/w) to 99% (w/w)-50 (w/w), and a more preferred ratio between the hydrophobic drug and the modified hydrophobic excipient is 1:1 to 1:5.

In a further development of the fifth aspect of the present application, the surfactant may be any pharmaceutical excipient belonging to the class of surfactants.

In a further development of the fifth aspect of the present application, the surfactant may be any pharmaceutical excipient of the class of surfactants having a hydrophilic-lipophilic balance (HLB) value in the range of 0 to 40.

In a further development of the fifth aspect of the present application, the surfactant can be any small molecule or large molecule pharmaceutical excipient with the functions of solubilizing or emulsifying or wetting or foaming agent or defoaming agent or detergent.

In a further development of the fifth aspect of the present application, the surfactant can be any small molecule or large molecule pharmaceutical excipient with the function of stabilizing the nanometer structure.

In a further development of the fifth aspect of the present application, the surfactant may be a cationic or anionic or nonionic surfactant.

In a further development of the fifth aspect of the present application, the surfactant can be phospholipid or cholesterol, or fatty acid with the chain length of C8-C22, or fatty acid salt with the chain length of C8-C22, sucrose fatty acid ester, sorbitan fatty acid (spans), polysorbate (Tweens) polyoxyethylene fatty acid ester (Myrij), polyoxyethylene fatty alcohol ether, or PEG-cholesterol derivative with different chain lengths, PEG-vitamin E succinate with different chain lengths, or PEG-phospholipid derivative with different chain lengths, or PEG-diglyceride derivative with different chain lengths, or any natural polymer pharmaceutical excipient or synthetic polymer pharmaceutical excipient with surface activity.

In a further development of the fifth aspect of the present application, the surfactant phospholipid can be any one selected from a group consisting of the following compounds, but not limited to, phosphatidylcholine (PC), Phosphatidylglycerol (PG), phosphatidylethanolamine (PE), phosphatidylserine (PS), phosphatidic acid (PA), phosphatidylinositol (PI), eggphosphatidylcholine (EPC), egg phosphatidylglycerol (EPG), phosphatidylethanolamine (EPE), eggphosphatidylserine (EPS), egg phosphatidic acid (EPA), (egg phosphatidylinositol (EPI), soy phosphatidylcholine (SPC), soy phosphatidylglycerol (SPG), soyphosphatidylethanolamine (SPE), soy phosphatidylserine (SPS), (soy phosphatidic acid SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soyphosphatidylcholine (HSPC), distearoylphosphatidylcholine (DSPC), distearoylphosphatidylglycerol (DSPG), dioleoylphosphatidylethanolamine (DSPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), distearoylphosphatidylethanolamine (DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidicacid (DPPA), 1,2-dioleoyl-snglycero-3-phosphatidic acid (DOPA), dimyristoylphosphatidic acid (DMPA), distearoylphosphatidic acid (DSPA), dipalmitoylphosphatidylinositol (DPPI), 1,2-dioleoylsn-glycero-3-phosphatidylinositol (DOPI), dimyristoylphosphatidylinositol (DMPI), distearoylphosphatidylinositol (DSPI), and mixtures of the foregoing phospholipids.

In a further development of the fifth aspect of the present application, the polyethylene glycol (PEG) with different chain lengths—the lipid derivative with the chain length of C8-C22, can be any surfactant formed by connecting PEG with the chain length of 1-1000 repeating units and lipid with the chain length of C8-C22 by ester bonds or ether bonds or amide bonds.

In a further development of the fifth aspect of the present application, the PEG-phospholipid derivatives with different chain lengths are surfactants formed by connecting PEG with the chain length of 1-1000 repeating units and natural or synthetic phospholipid by an ester bond, an amide bond or a carbamoyl bond.

In a further development of the fifth aspect of the present application, in the PEG-phospholipid derivatives with different chain lengths, prepared by connecting PEG with the chain length of 1-1000 repeating units with natural or synthetic phospholipids through ester bonds or amide bonds or carbamoyl bonds to obtain the surfactants, the natural or synthetic phospholipids can be natural or synthetic phospholipids with a carbon chain length of 12-22.

In a further development of the fifth aspect of the present application, in the PEG-phospholipid derivatives with different chain lengths, prepared by connecting PEG with the chain length of 1-1000 repeating units with natural or synthetic phospholipids through ester bonds or amide bonds or carbamoyl bonds to obtain the surfactants, the natural or synthetic phospholipids can be natural or synthetic phospholipid of saturated or unsaturated lipid chains with a carbon chain length of 12-22.

In a further development of the fifth aspect of the present application, in the PEG-phospholipid derivatives with different chain lengths, prepared by connecting PEG with the chain length of 1-1000 repeating units with natural or synthetic phospholipids through ester bonds or amide bonds or carbamoyl bonds to obtain the surfactants, the natural or synthetic phospholipids can be natural or synthetic cephalin.

In a further development of the fifth aspect of the present application, the natural polymer pharmaceutical excipient or synthetic polymer pharmaceutical excipient surfactant can be polysaccharide or polysaccharide derivative or polyoxyethylene-polyoxypropylene (poloxamer) or protein with surface activity.

In a further development of the fifth aspect of the present application, the pharmaceutical excipient surfactant can be a single pharmaceutical excipient or a combination of multiple pharmaceutical excipient surfactants by different proportions.

In a further development of the fifth aspect of the present application, the surfactant can be lecithin or cholesterol or PEG-phospholipid derivative single pharmaceutical excipient or a combination of multiple pharmaceutical excipient surfactants by different proportions.

In a further development of the fifth aspect of the present application, the surfactant can be combinations of lecithin and PEG-cephalin derivative by different proportions.

In the above technical solution, the blank fat emulsion can be prepared by adopting the modified hydrophobic excipient as the oil phase, in combintion with a combination of lecithin and PEG-cephalin derivatives by different proportions.

In addition, In the above technical solution, the drug-loaded fat emulsion can be prepared by adopting the modified hydrophobic excipient as the oil phase, in combination with a combination of the hydrophobic medicament, lecithin and the PEG-cephalin derivative by different proportions, so as to improve the drug-loaded amount and the stability of the drug-loaded fat emulsion.

In a further development of the fifth aspect of the present application, the proportion of the hydrophobic excipient—the hydrophobic drug to the surface active excipient is (X+Y):Z, and Z %=100−(X+Y).

In a further development of the fifth aspect of the present application, the proportion of the hydrophobic excipient—the hydrophobic drug to the surface active excipient is (X+Y):Z=(0-50%):(100-50%).

In the above technical solution, the drug-loaded fat emulsion can be prepared by different physical methods by adopting the modified hydrophobic excipient as the oil phase, in combination with a combination of hydrophobic medicament, the lecithin and PEG-cephalin derivatives by different proportions.

In a further development of the fifth aspect of the present application, the preparation method of the drug-loaded fat emulsion includes one or a combination of high-speed shearing, phase transition, high-pressure homogenization, micro-jet and micro-fluidic methods.

In the above technical solution, the mixture of the hydrated hydrophobic excipient, the hydrophobic drug and the surface active excipient are treated by one or a combination of physical methods, so as to achieve the effect of effectively and controllably reducing the diameter of the fat emulsion.

In conclusion, the present application has the following beneficial effects.

1. The modified hydrophobic excipient has a π-π function by introducing an substituent group with an aromatic ring, so that the modified hydrophobic excipient and the drug containing the aromatic group can have aromatic ring stacking. Further, the carbamoyl group and the amide group on the modified hydrophobic excipient can have a non-covalent physical action with the drug through hydrogen bonds, so that the solubility of the drug can be increased, and the stability of the drug-loaded fat emulsion can be improved.
2. The modified hydrophobic excipient can have a non-covalent physical action with the drug through π-π and hydrogen bonds, so that the modified hydrophobic excipient has a wider application range of drug loading.
3. The carboxyl on the amino acid derivative reacts with the hydroxyl on the hydrophobic natural excipient with one to three hydroxyl groups or the hydrophobic synthetic excipient with one to three hydroxyl groups to form an ester bond. This is favorable for increasing the hydrophobicity of the hydrophobic excipient, and, at the same time, favorable for introducing an aromatic substituent group and a carbamoyl group or an amide group onto the hydrophobic excipient. This is also favorable for the hydrophobic excipient and the drug containing the aromatic group to be combined with each other through π-π aromatic ring stacking and non-covalent physical action such as hydrogen bond, favorable for increasing the solubility of the drug to improve the stability of the drug-loaded fat emulsion, and is favorable for expanding the application range of the hydrophobic excipient.
4. Firstly preparing an amino acid ester of the hydrophobic excipient and then introducing the protected amino acid by utilizing the activated ester of the N-hydroxysuccinimide or the 1-hydroxybenzotriazole for protecting the amino acid is beneficial for alleviating the problem of incomplete coupling reaction due to steric hindrance, and at the same time, is favorable for forming the hydrophobic excipient modified by the amino acid derivatives.
5. Using the hydrophobic excipient as an oil phase excipient for preparing the drug-loaded fat emulsion facilitates increasing the solubility of a drug, and at the same time, increasing the drug-loaded amount of the drug-loaded fat emulsion, and in turn the stability of the drug-loaded fat emulsion.

DETAILED DESCRIPTION

The present application will be described in further detail with reference to examples.

Example 1

A preparation method of a modified hydrophobic excipient was performed as follows: 9.34 g of castor oil (10 mmol), 29.5 g of N-fluorenylmethoxycarbonyl-N'-tert-butoxycarbonyl-L-lysine (60 mmol), 366 mg of 4-dimethylaminopyridine (DMAP) (3 mmol) were added into a 250 ml flask, then added with 12.4 g of dicyclohexylcarbodiimide (DCC) dissolved in 50 ml of anhydrous dichloromethane (60 mmol) and reacted at room temperature under dark conditions for three days. After the reaction being completed, as indicated by TLC analysis, the reaction mixture was filtered to remove the precipitate, then spin-dried, and purified by conventional purification to obtain a yellowish transparent viscous oily substance, which was cooled to obtain a glassy transparent solid as a modified hydrophobic excipient. The reaction formula was shown below. Castor oil is usually a mixture of triglycerides with different ricinoleic acid content (n=0-3), and molecular formula thereof cannot be accurately illustrated. The following reaction formula, taking n=3 as an example, is used to illustrate the method principle of the present application without limiting the present application.

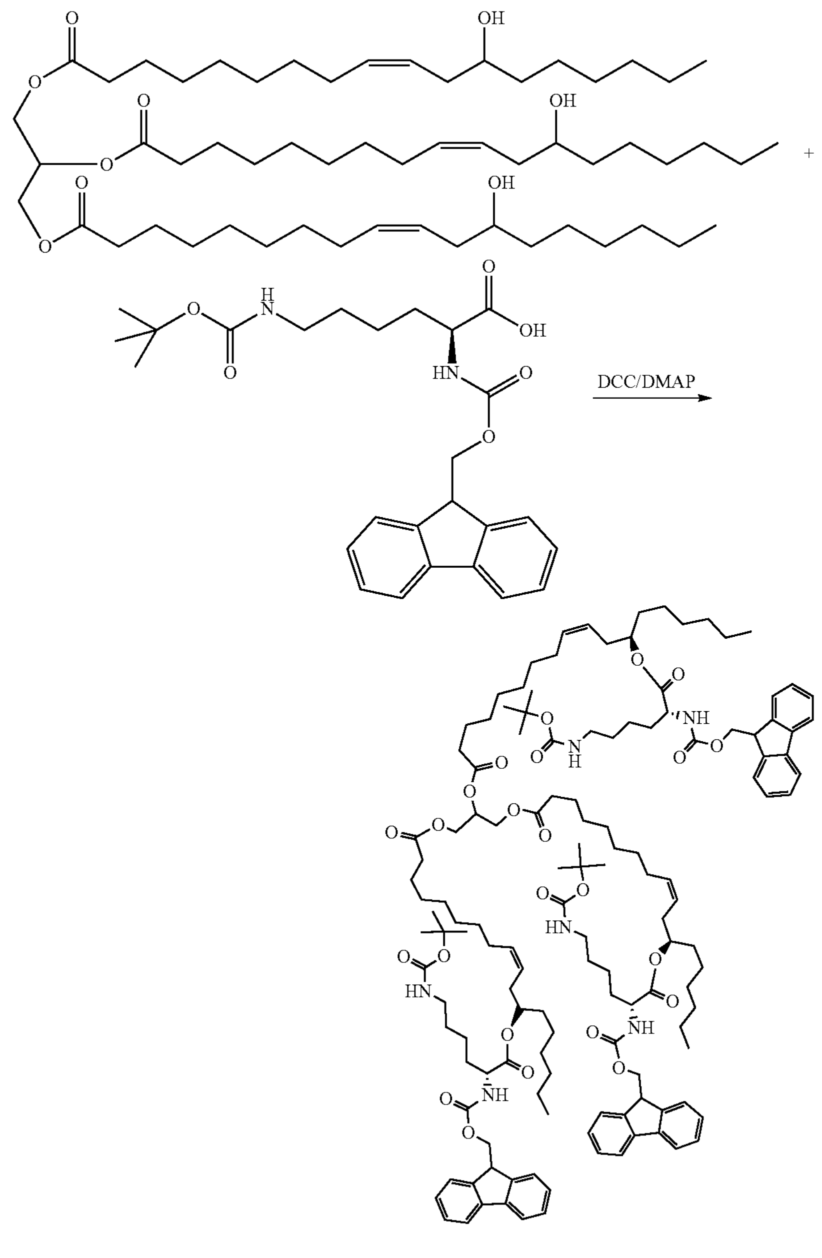

Example 2

A preparation method of a hydrophobic excipient was performed as follows:

A-1, castor oil-O-glycine triester was esterified by N-tert-butoxycarbonylglycine, and then was subjected to acidification deprotection by the following synthetic route:

9.34 g of castor oil (10 mmol), 7.2 g of N-t-butoxycarbonylglycine (45 mmol), and 366 mg of 4-dimethylaminopyridine (DMAP) (3 mmol) were added into a 250 ml flask, then added with 12.4 g of N, N'-dicyclohexylcarbodiimide (DCC) (60 mmol) dissolved in 50 ml of anhydrous dichloromethane, and reacted at room temperature under dark conditions for two days. After the reaction being completed, as indicated by TLC analysis, the reaction mixture was filtered to remove the precipitate, then spin-dried, and purified by conventional purification to obtain a colorless, transparent viscous oil, that is, the intermediate I, castor oil-O—(N-t-butoxycarbonyl-glycine) triester.

The intermediate I was dissolved in 40 ml of dichloromethane (DCM), then added with 40 ml of trifluoroacetic acid (TFA), and reacted at room temperature for 4 hours, to remove the protecting group. After removing excessive trifluoroacetic acid by spinning, 60 ml of dichloromethane was added to dissolve the product, then added with 10 g anhydrous sodium carbonate powder, and stirred for three days to obtain intermediate II, which was castor oil-O-glycine triester. The reaction formula was shown below. Castor oil is usually a mixture of triglycerides with different ricinoleic acid content (n=0-3), and molecular formula thereof cannot be accurately illustrated. The following reaction formula, taking n=3 as an example, is used to illustrate the method principle of the present application without limiting the present application.

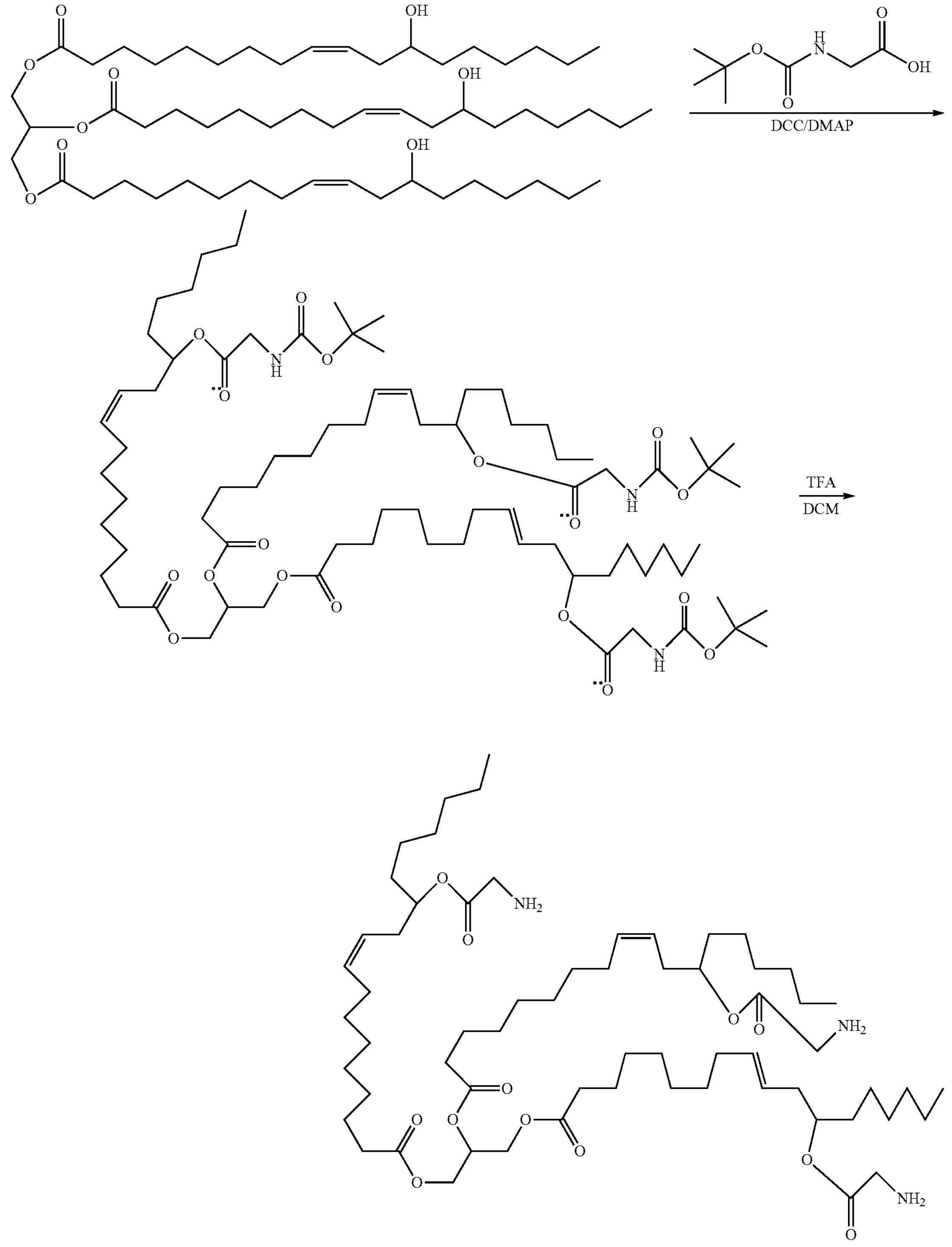

Or A-2, the castor oil-O-glycine triester were esterified by N-benzyloxycarbonyl glycine and then synthesized by a catalytic hydrogenation deprotection synthetic route, which included the following steps:

9.34 g of castor oil (10 mmol), 8.6 g N-benzyloxycarbonylglycine (45 mmol), and 366 mg of 4-dimethylaminopyridine (DMAP) (3 mmol) were added to a 250 ml flask, then added with 12.4 g (60 mmol) of dicyclohexylcarbodiimide (DCC) dissolved in 50 ml of anhydrous dichloromethane, and reacted for two days at room temperature under dark conditions. After the reaction being completed, as indicated by TLC analysis, the reaction mixture was filtered to remove the precipitate, then spin-dried, and purified by conventional purification to obtain a colorless, transparent viscous oil, that is, the intermediate I, which was castor oil-O—(N-benzyloxycarbonylglycine) triester.

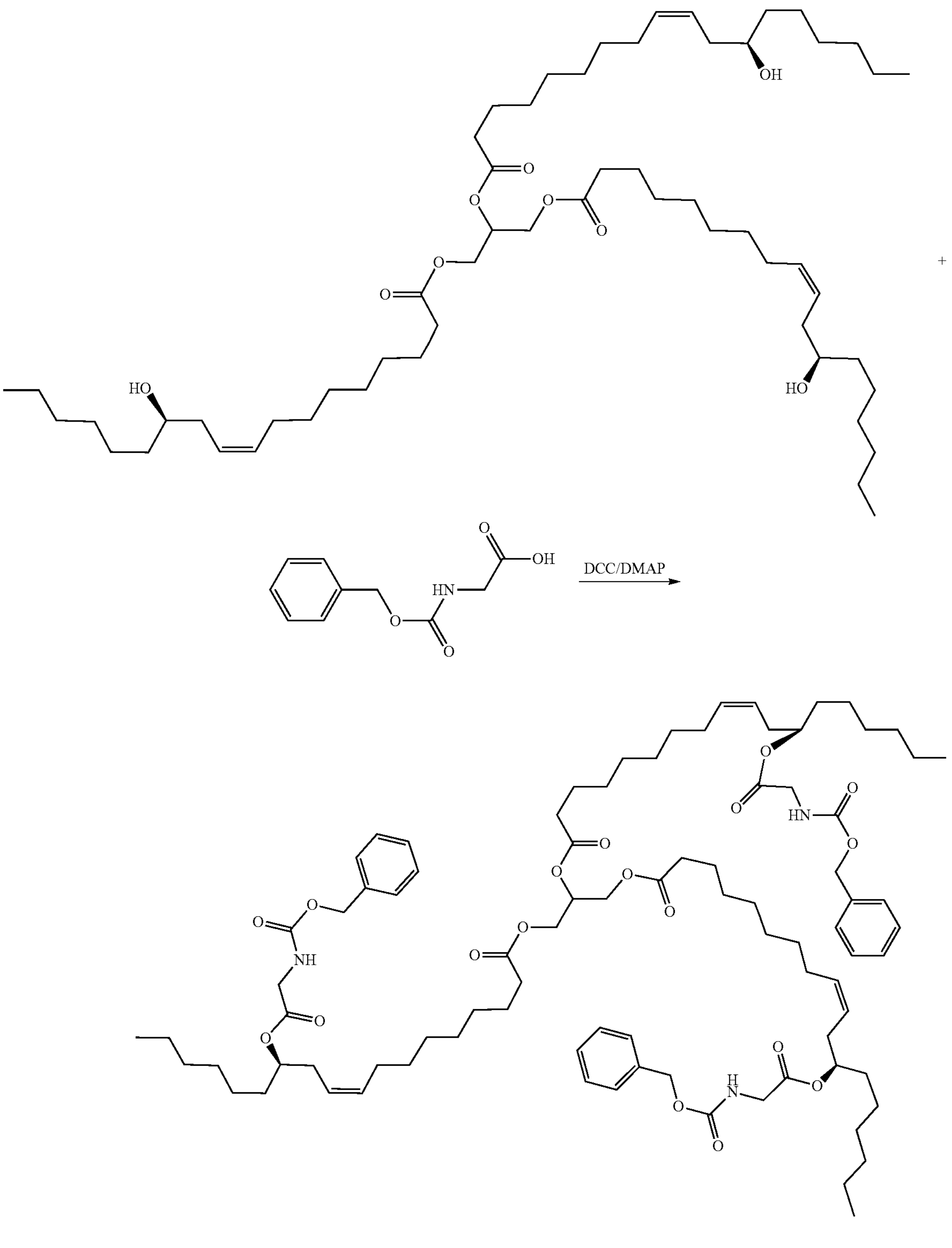

In a catalytic hydrogenation pressure reactor, 15 g of castor oil-O—(N-benzyloxy-carbonylglycine) triester was added, and then added with 40 ml of methanol and lml of glacial acetic acid (HOAC). The mixture was sufficiently stirred and dissolved, added with about 600 mg of 5% palladium on carbon (Pt/C), the headspace air was replaced with hydrogen under stirring, the hydrogen pressure was increased to 5 atm, the reaction was carried out at room temperature for 4 hours, the benzyloxycarbonyl protecting group was removed, and the excess acetic acid was removed by rotary drying to obtain intermediate II, which was castor oil-O-glycine triester acetate. The reaction formula was shown below. Castor oil is usually a mixture of triglycerides with different ricinoleic acid content (n=0-3), and molecular formula thereof cannot be accurately illustrated. The following reaction formula, taking n=3 as an example, is used to illustrate the method principle of the present application without limiting the present application.

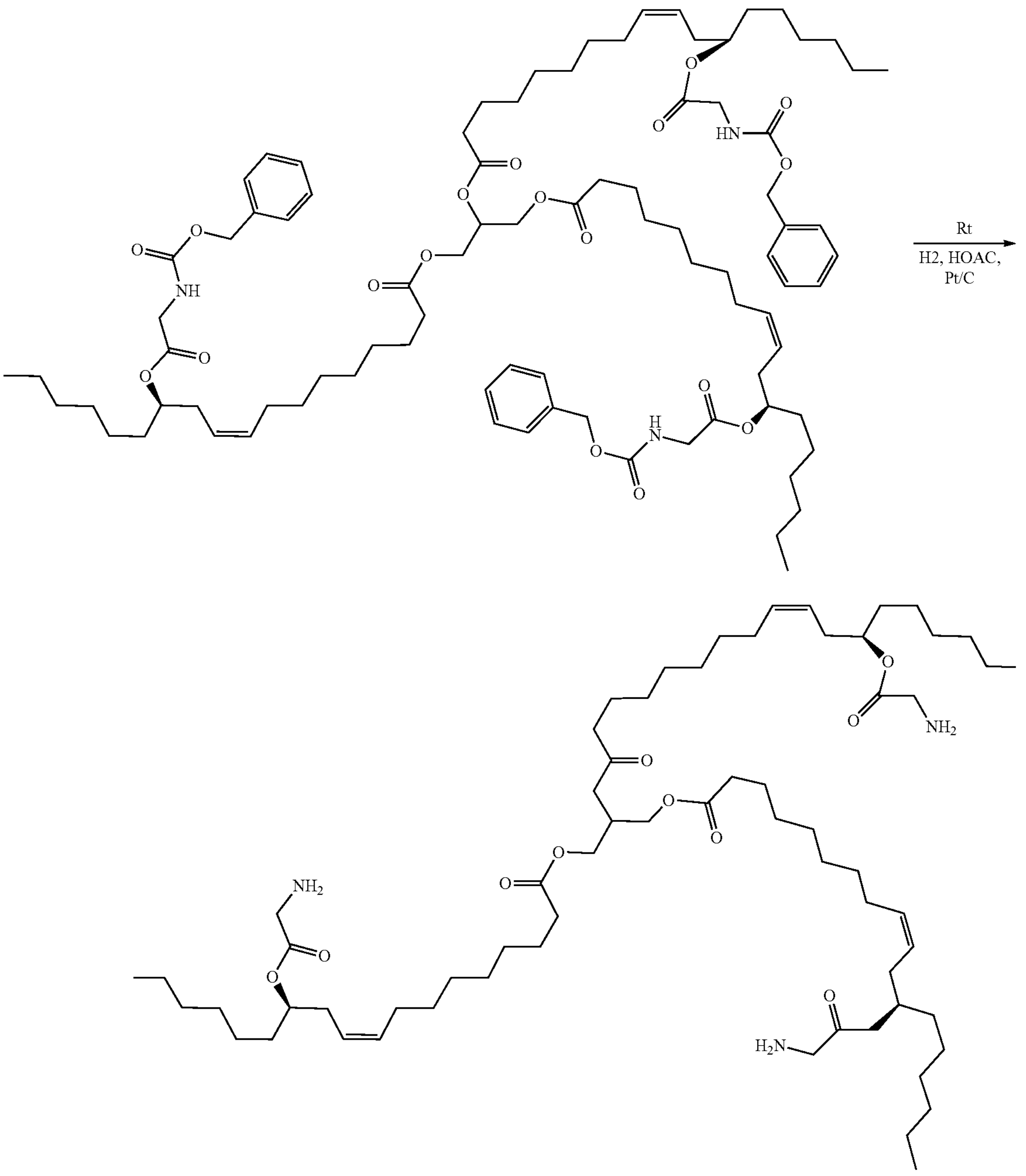

B. The synthesis of N-fluorenylmethoxycarbonyl-N'-tert-butoxycarbonyl-L-lysine-N-hydroxysuccinimide ester was performed as follows:

24 g of N-fluorenylmethoxycarbonyl-N'-tert-butoxycarbonyl-L-lysine (50 mmol) and 5.6 g (50 mmol) of N-hydroxysuccinimidein were added to a 250 ml flask, and the starting material was dissolved in 40 ml of tetrahydrofuran (THF), then added with 12.4 g (60 mmol) of dicyclohexylcarbodiimide (DCC) dissolved in 50 ml of methylene chloride, and reacted at room temperature for 1 hour. The reaction was filtered to remove the precipitate and then dried by spin-drying to obtain intermediate III, which was N-fluorenylmethoxycarbonyl-N'-tert-butylcarbonyl-L-lysine-N-hydroxysuccinimide ester. The reaction formula was shown below.

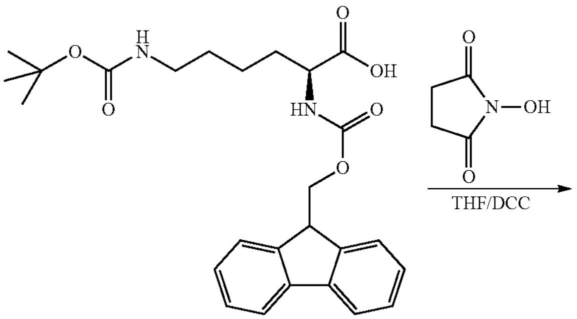

-continued

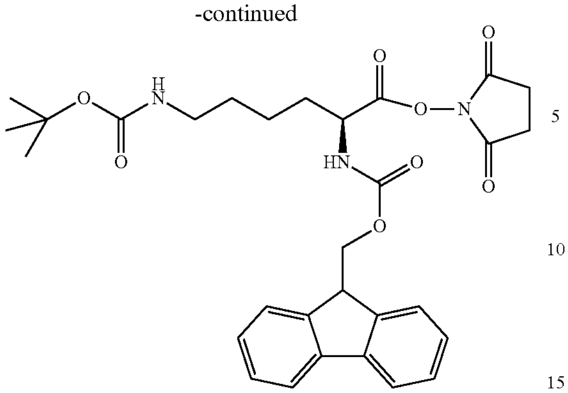

C. The synthesis of the hydrophobic excipients was performed as follows:

10.5 g of the intermediate II was dissolved in 100 ml of anhydrous dichloromethane, added with 15 ml of triethylamine (TEA), then added with 30 g of the intermediate III dissolved in 50 ml of dichloromethane, and reacted for three days under a dark condition. After the reaction being completed, as indicated by TLC analysis, the reaction mixture was filtered to remove the precipitate, then spin-dried, and purified by conventional purification to obtain a yellowish transparent viscous oily substance, which was cooled to obtain a glassy transparent solid as a modified hydrophobic excipient. The reaction formula was shown below.

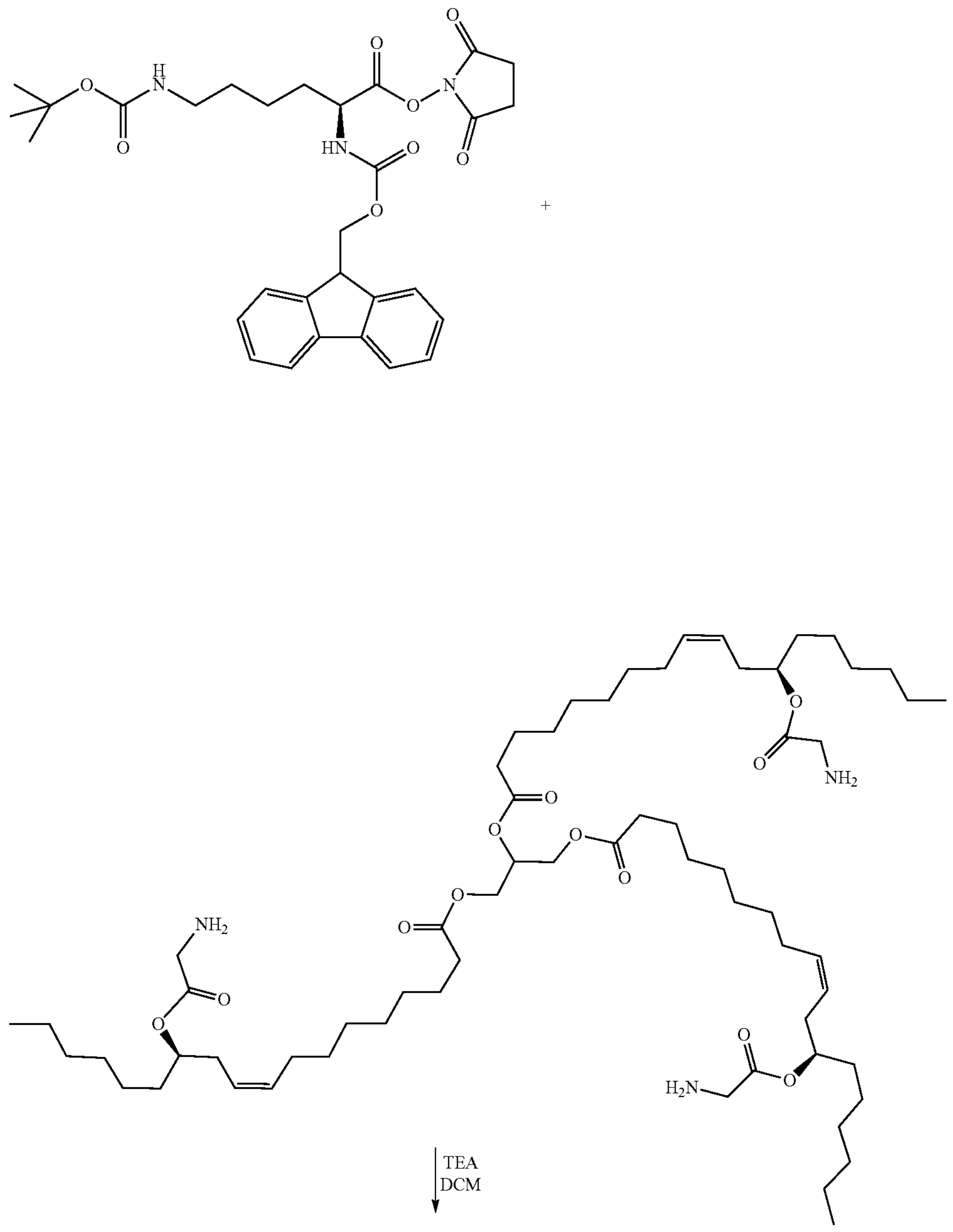

-continued

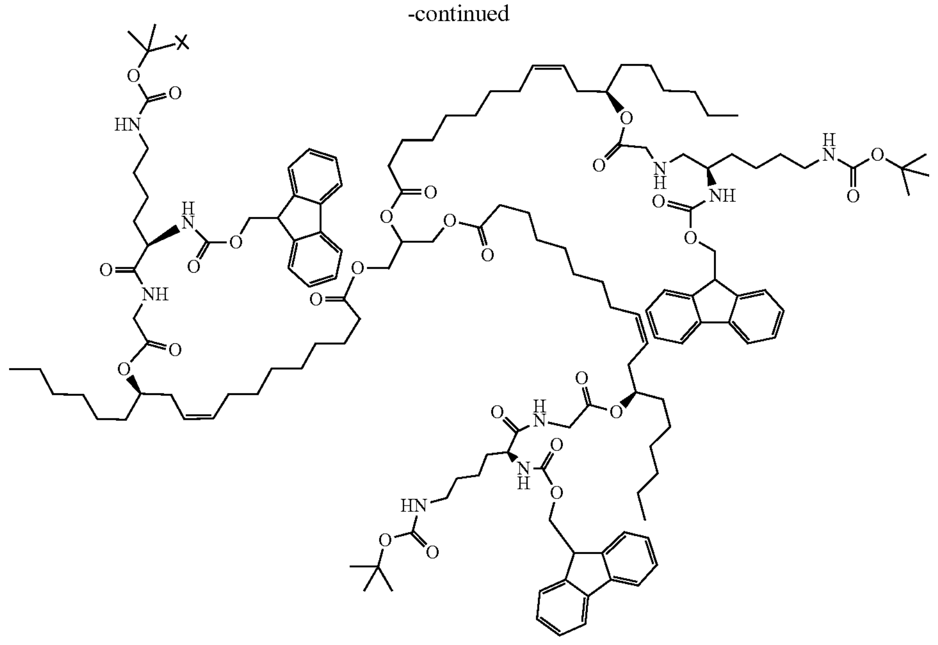

Example 3

A preparation method of a hydrophobic excipient was performed as follows:

A. the synthesis of hydrogenated castor oil-O-glycine triester was performed as follows: 9.36 g of hydrogenated castor oil (10 mmol), 7.2 g of N-tert-butoxycarbonylglycine (45 mmol), 366 mg of 4-dimethylaminopyridine (DMAP) (3 mmol) were dissolved in 100 ml of anhydrous dichloromethane (DCM) in a 250 ml flask, then added with 10.3 g (50 mmol) of dicyclohexyl-carbodiimide (DCC) dissolved in 50 ml of anhydrous dichloromethane, refluxed at 45° C. and reacted for two days under dark conditions. After the reaction being completed, as indicated by TLC analysis, the reaction mixture was filtered to remove the precipitate, and then spin-dried to provide a residue. The residue was recrystallized from ethyl acetate to obtain a slightly yellowish transparent oily substance, which was cooled to obtain white crystals, that is, the intermediate I, which was hydrogenated castor oil-O—(N-tert-butoxycarbonylglycine) triester.

The intermediate I was dissolved in 40 ml of dichloromethane, added with 40 ml of trifluoroacetic acid (TFA), and reacted at room temperature for 4 hours, to remove the protecting group. After removing excessive trifluoroacetic acid by spinning, 60 ml of dichloromethane was added to dissolve the product, the added with 10 g of anhydrous sodium bicarbonate powder, and stirred for three days to obtain the intermediate II, which was hydrogenated castor oil-O-glycine triester. The reaction formula was shown below. Castor oil is usually a mixture, and molecular formula thereof cannot be accurately illustrated. The following reaction formula, taking n=3 as an example, is used to illustrate the method principle of the present application without limiting the present application.

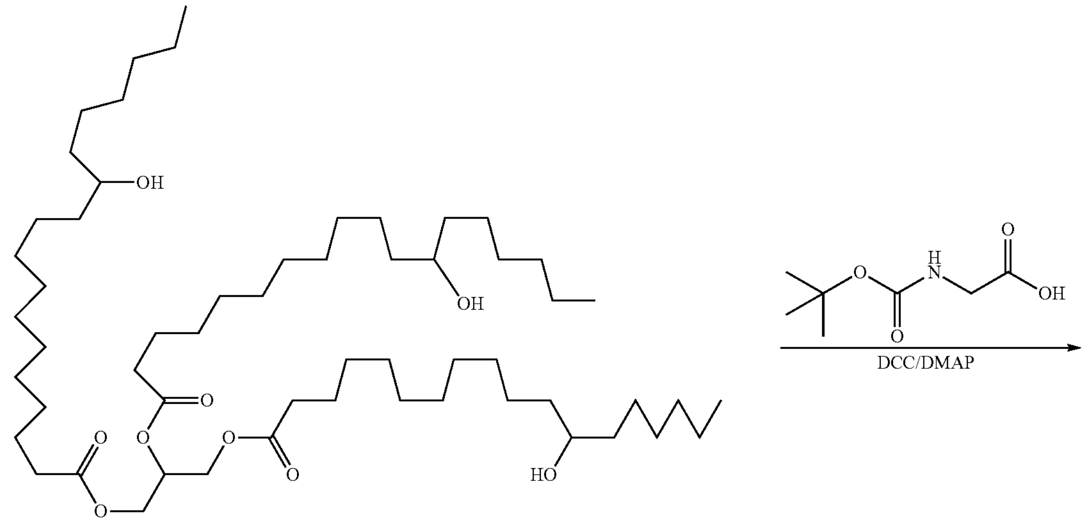

-continued

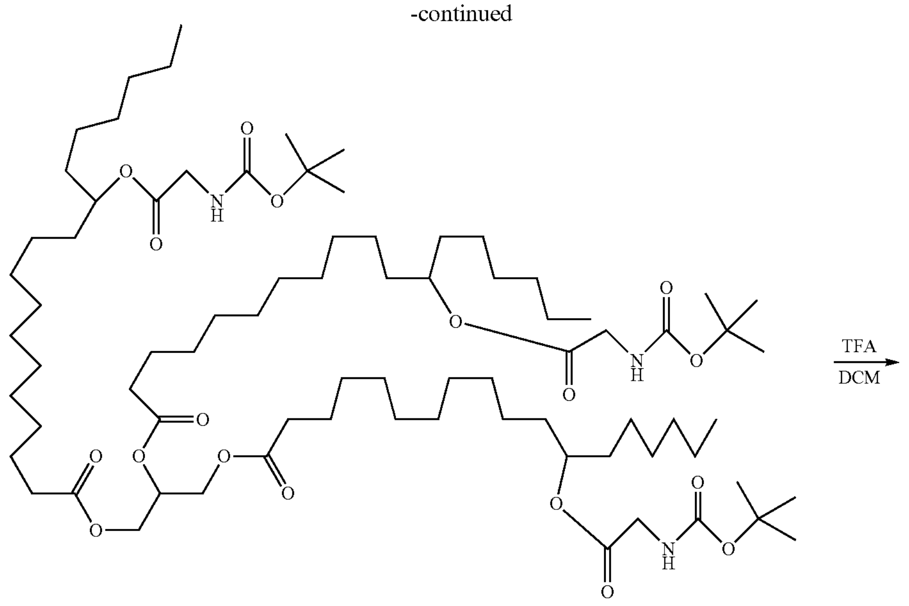

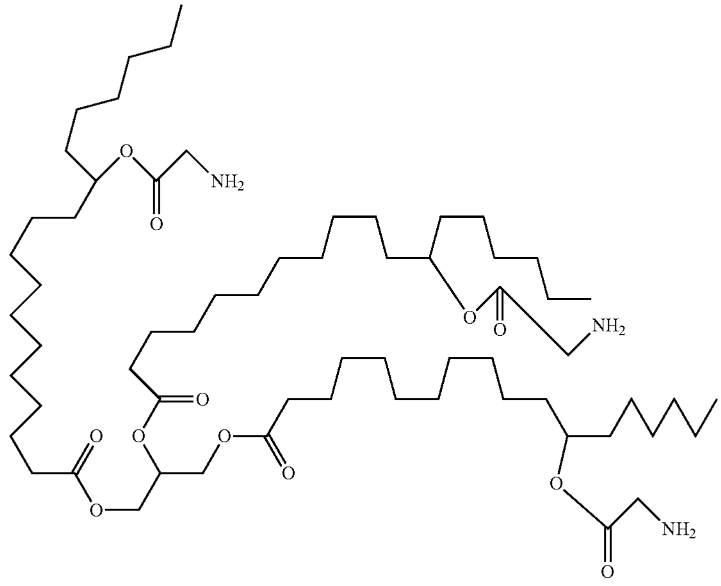

B. The synthesis of N-fluorenylmethoxycarbonyl-N'-tert-butoxycarbonyl-L-lysine-N-hydroxysuccinimide ester was performed as follows:

24 g of N-fluorenylmethoxycarbonyl-N'-tert-butoxycarbonyl-L-lysine (50 mmol) and 5.6 g (50 mmol) of N-hydroxysuccinimide in were added to a 250 ml flask, dissolved in 40 ml of anhydrous tetrahydrofuran (THF), then added with 12.4 g (60 mmol) of dicyclohexylcarbodiimide (DCC) dissolved in 50 ml of methylene chloride, reacted at room temperature for 1 hour, filtered to remove the precipitate and then dried by spin-drying to obtain the intermediate III which was N-fluorenylmethoxycarbonyl-N'-tert-butylcarbonyl-L-lysine-N-hydroxysuccinimide ester. The reaction formula was shown below.

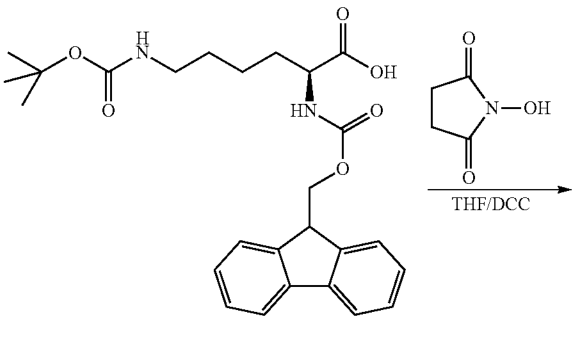

-continued

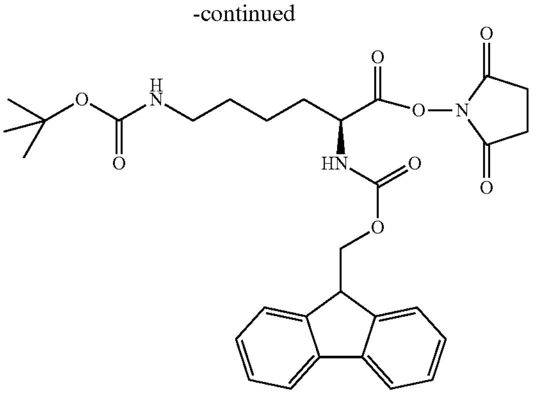

C. The synthesis of the modified hydrophobic excipient was performed as follows: the intermediate II was dissolved in 100 ml of anhydrous dichloromethane, added with 15 ml of triethylamine (TEA), then added with the intermediate III dissolved in 50 ml of dichloromethane (DCM), refluxed at 45° C., and reacted for three days under a dark condition. After the reaction being completed, as indicated by TLC analysis, the reaction mixture was filtered to remove the precipitate, then spin-dried to obtain a residue. The residue was recrystallized from ethyl acetate, to obtain a slightly yellowish transparent oily substance, which was cooled to obtain white crystals, as the hydrophobic excipient. The reaction formula was shown below.

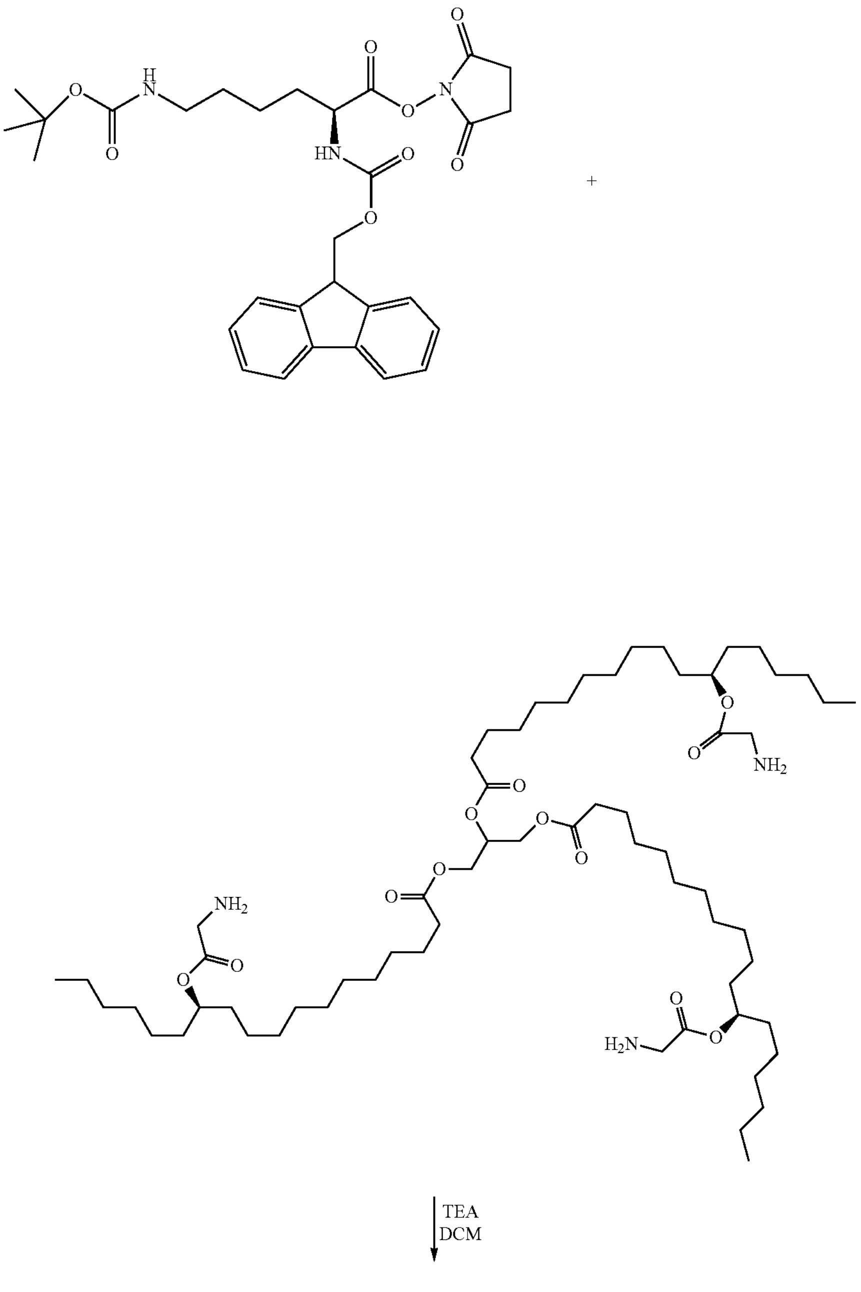

-continued

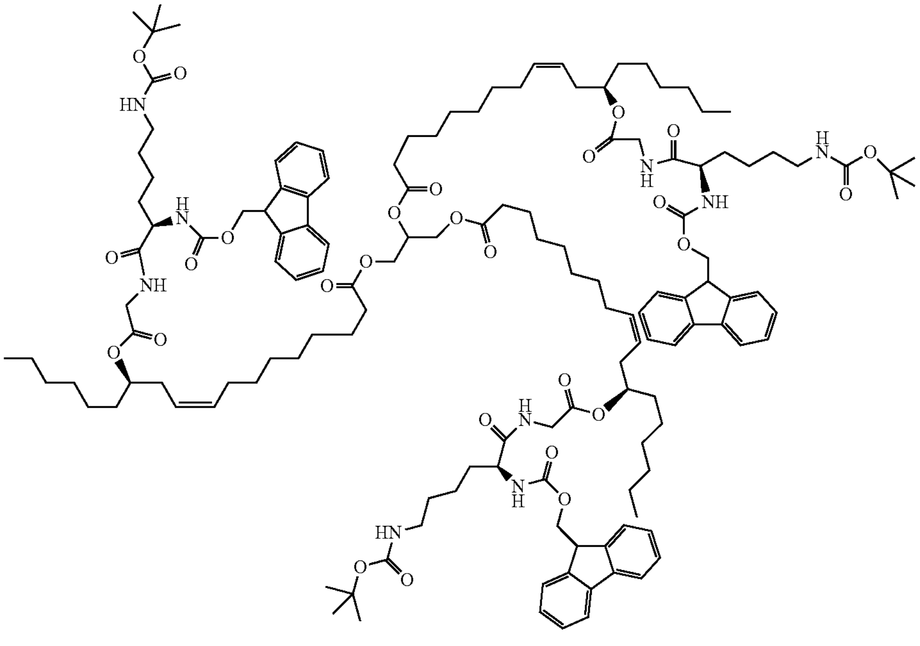 [SMILES: CCCCCC[C@H](C/C=C\CCCCCCCC(=O)OCC(COC(=O)CCCCCCC/C=C\C[C@@H](CCCCCC)OC(=O)CNC(=O)[C@@H](CCCCNC(=O)OC(C)(C)C)NC(=O)OCC1c2ccccc2-c2ccccc21)OC(=O)CCCCCCC/C=C\C[C@@H](CCCCCC)OC(=O)CNC(=O)[C@@H](CCCCNC(=O)OC(C)(C)C)NC(=O)OCC1c2ccccc2-c2ccccc21)OC(=O)CNC(=O)[C@H](CCCCNC(=O)OC(C)(C)C)NC(=O)OCC1c2ccccc2-c2ccccc21]

Example 4

A preparation method of a hydrophobic excipient was performed as follows:

A. the synthesis of the cholesterol oleamide-O-glycine triester was performed as follows: 3.82 g of cholic acid (10 mmol) and 1.2 g of N-hydroxysuccinimide (11 mmol) were added to a 250 ml flask, dissolved in 40 ml of anhydrous tetrahydrofuran (THF), then added with 2.3 g of dicyclohexylcarbodiimide (DCC) (11 mmol), and reacted at room temperature for 2 hours to form cholic acid-N-hydroxysuccinimide active ester. After the reaction being completed, as indicated by TLC analysis, the reaction was added with 2.8 g of oleylamine (10 mmol) and 1.5 ml of triethylamine (TEA) (10 mmol), and reacted overnight. After the reaction being completed, as indicated by TLC analysis, the reaction mixture was filtered to remove the precipitate, then spin-dried, and purified by conventional purification to obtain a colorless, transparent viscous oil, as the cholesterol oleamide. The reaction formula was shown below.

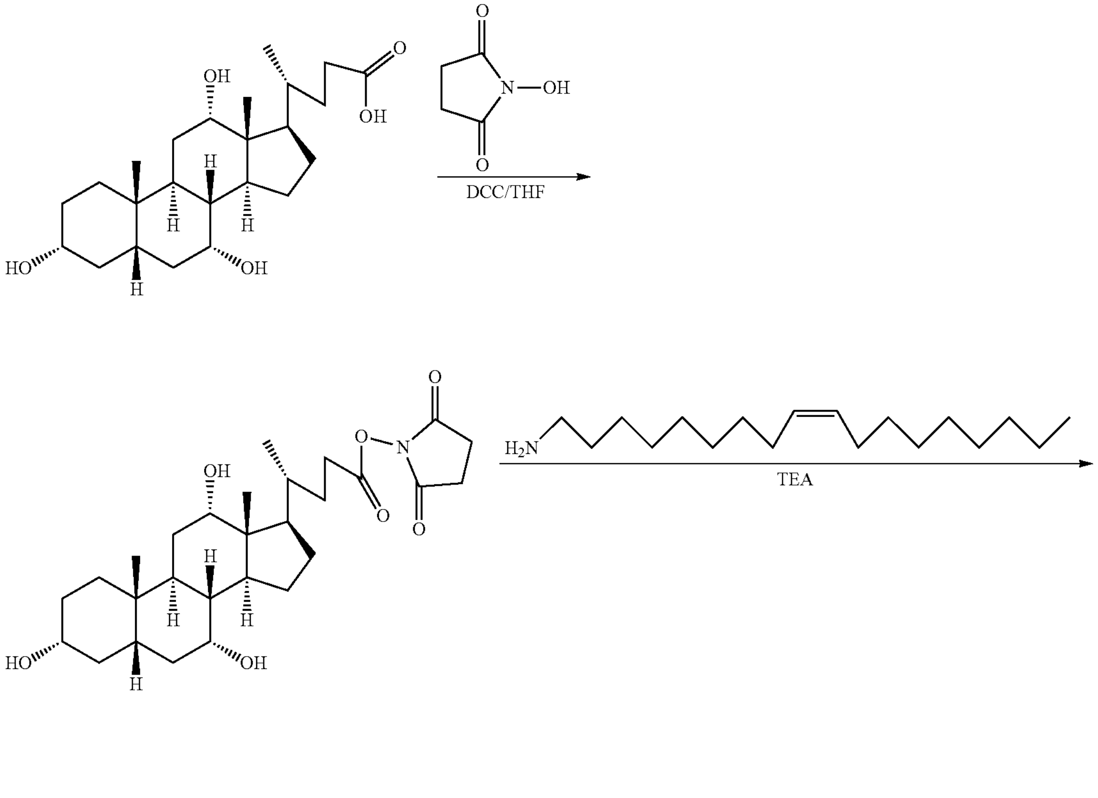

-continued

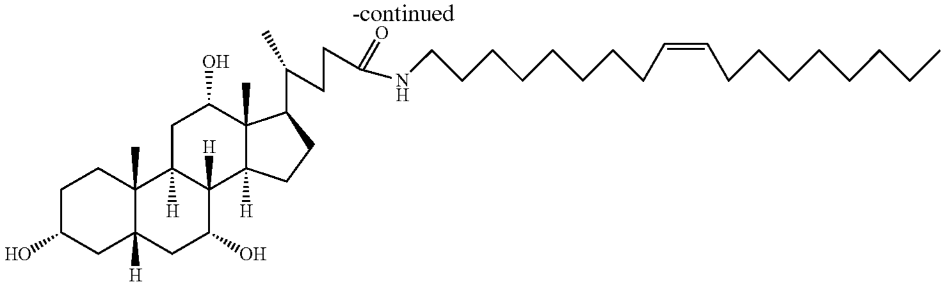

7.2 g N-tert-butoxycarbonylglycine (45 mmol) was added to a 100 ml flask, dissolved in 100 ml of anhydrous dichloromethane (DCM), and added with 5.4 g (25 mmol) of dicyclohexyl-carbodiimide (DCC) dissolved in 50 ml of anhydrous dichloromethane, and reacted at room temperature for 0.5 h to form N-tert-butoxycarbonylglycine anhydride. The reaction formula was shown below.

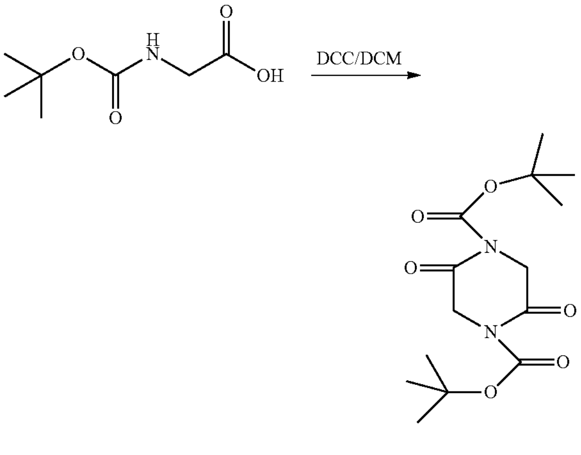

Cholesterol oleamide produced in the above reaction and 122 mg of 4-dimethylaminopyridine (DMAP) (lmmol) were dissolved in 40 ml of anhydrous dichloro-methane (DCM), then added with N-tert-butoxycarbonylglycine anhydride produced in the above reaction, and reacted for 48 hours. After the reaction being completed, as indicated by TLC analysis, the intermediate I was obtained, which was cholesterol oleamide-O—(N-tert-butoxycarbonylglycine) triester.

The intermediate I was dissolved in 40 ml of dichloromethane, then added with 40 ml of trifluoroacetic acid (TFA), and reacted at room temperature for 4 h, to remove protecting groups. After removing excessive trifluoroacetic acid by spinning, the obtained product was dissolved in 60 ml of dichloromethane, then added with 10 g of anhydrous sodium bicarbonate powder, and stirred for three days to obtain the intermediate II, which was cholestyryl oleylamine-O-glycine triester. The reaction formula was shown below. The reaction formula was shown below.

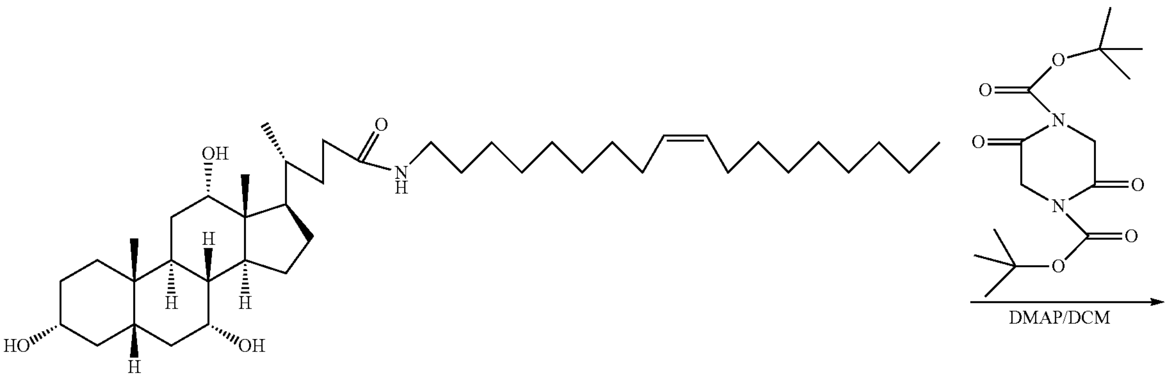

-continued

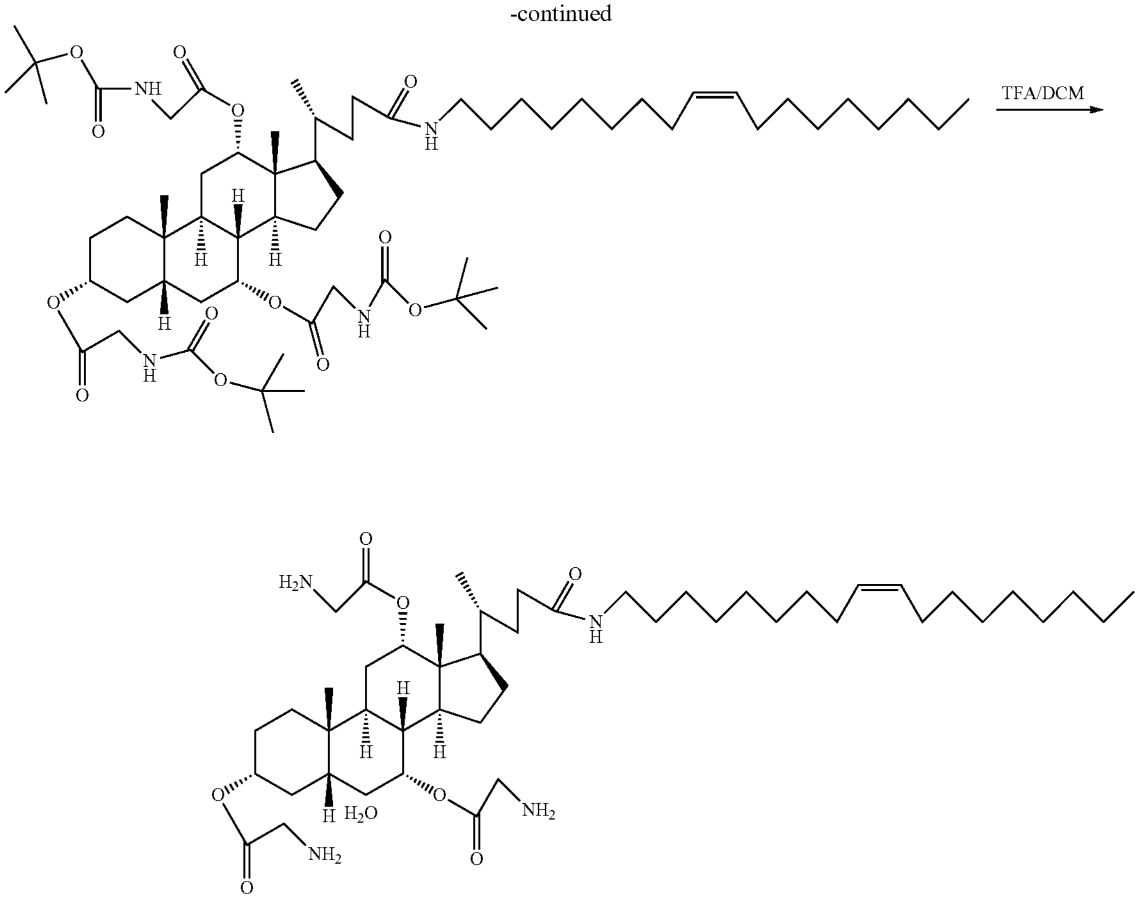

B. The synthesis of N-fluorenylmethoxycarbonyl-N'-tert-butoxycarbonyl-L-lysine-N-hydroxysuccinimide ester was performed as follows:

24 g of N-fluorenylmethoxycarbonyl-N'-tert-butoxycarbonyl-L-lysine (50 mmol) and 5.6 g of N-hydroxysuccinimide (50 mmol) were dissolved in 40 ml of anhydrous tetrahydrofuran (THF) in a 250 ml flask, added with 12.4 g (60 mmol) of dicyclohexylcarbodiimide (DCC) dissolved in 50 ml of dichloromethane, reacted at room temperature for 1 hour, and the mixture was filtered to remove precipitates and then dried by spin-drying to obtain the intermediate III, which was N-fluorenylmethoxycarbonyl-N'-tert-butoxycarbonyl-L-lysine-N-hydroxysuccinimide ester. The reaction formula was shown below.

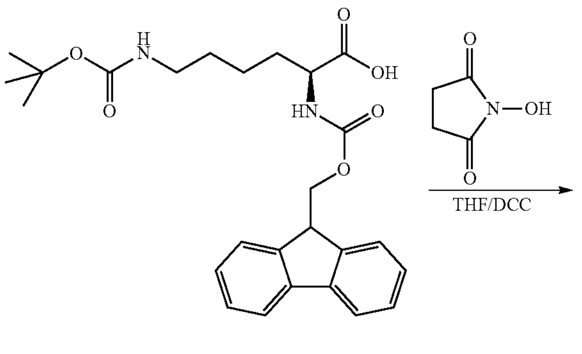

-continued

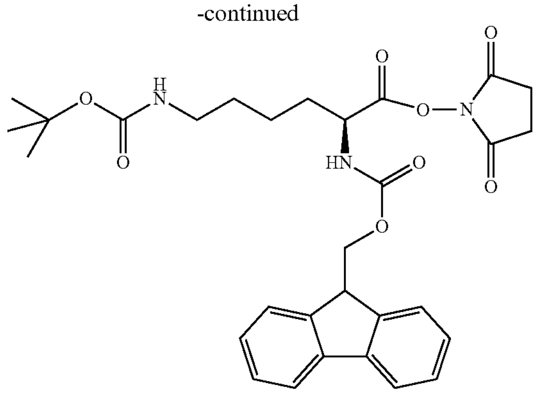

C. The synthesis of the hydrophobic excipients was performed as follows:

the intermediate II was dissolved in 100 ml of anhydrous dichloromethane, added with 15 ml of triethylamine (TEA), then added with the intermediate III dissolved in 50 ml of dichloromethane (DCM), and reacted for three days at room temperature under dark conditions. After the reaction being completed, as indicated by TLC analysis, the reaction mixture was filtered to remove the precipitate, then spin-dried, and purified by conventional purification to obtain a yellowish transparent viscous oily substance, which was cooled to obtain a glassy transparent solid as a modified hydrophobic excipient. The reaction formula was shown below.

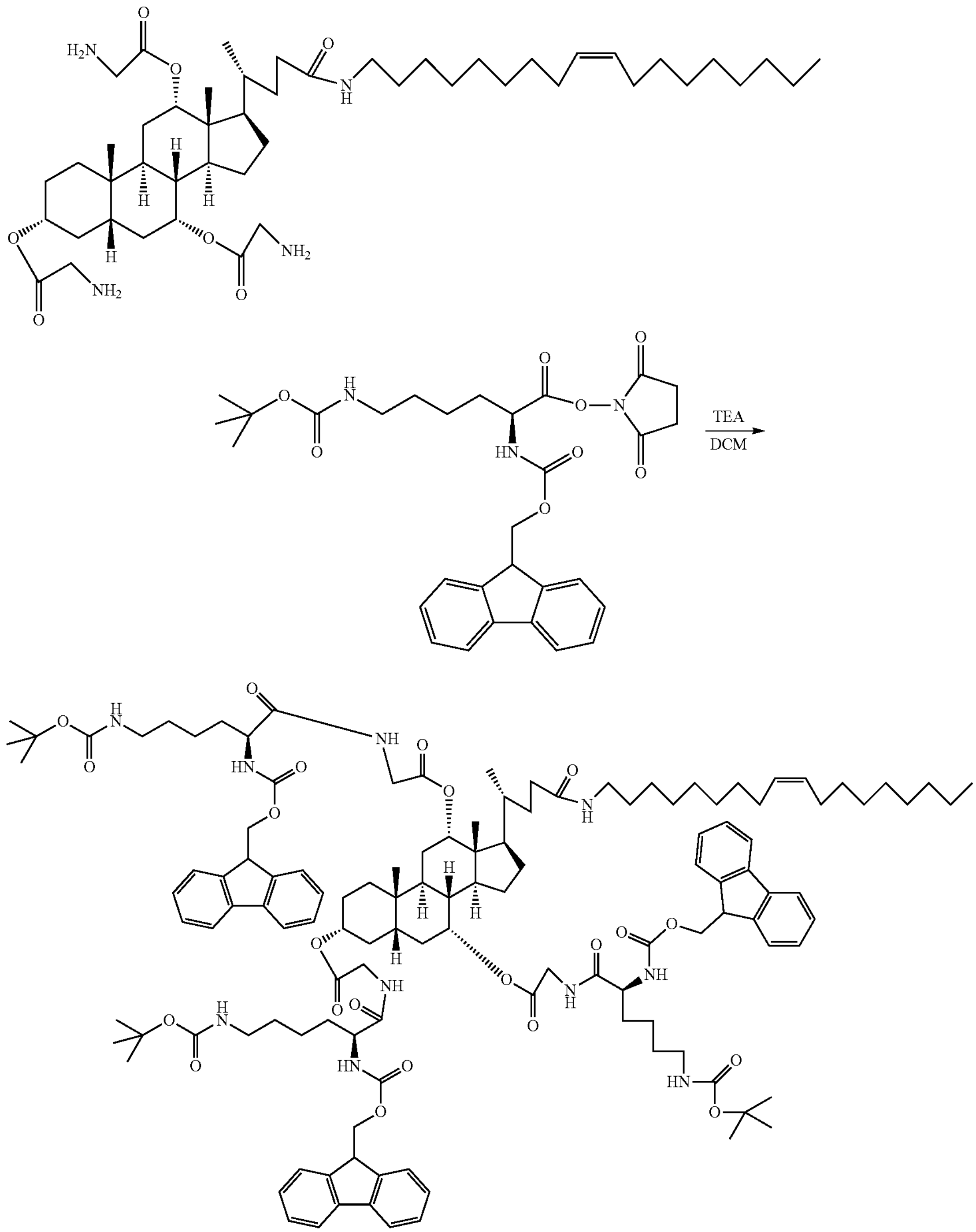

Example 5

The solubility of paclitaxel in olive oil, castor oil and the hydrophobic excipients prepared in the above examples was measured.

The specific experimental method was as follows. 0.5 ml of chloroform solution of olive oil, castor oil and the hydrophobic excipients prepared in the above examples were added to a 12 ml penicillin bottle, in which the mass percentage concentration of the chloroform solution of the hydrophobic excipients was 50%. The chloroform solution was mixed with 0.5 ml of chloroform, from which 0.5 ml of diluent was taken and two-fold serial dilution was performed by using chloroform. Then 0.5 ml of a chloroform solution of paclitaxel (10 mg/ml) was added to the above-mentioned sample after the two-fold serial dilution, and then left in a hood to be naturally volatilized overnight. Crystal formation in the dried sample was observed and recorded.

Experimental data of the solubility of paclitaxel in olive oil, castor oil and the hydrophobic excipients prepared in the above examples were shown in Table 1.

TABLE 1

| solubility of paclitaxel in olive oil, castor oil and hydrophobic excipients | | | | | |
|---|---|---|---|---|---|
| Hydrophobic excipient (mg) | Olive oil | Castor oil | Example 1 | Example 2 | Example 4 |
| 0.98 | + | + | + | + | + |
| 1.95 | + | + | + | + | + |
| 3.90 | + | + | + | + | + |
| 7.81 | + | + | +/− | − | +/− |
| 15.65 | + | + | − | − | − |
| 31.30 | + | + | − | − | − |
| 62.50 | + | + | − | − | − |
| 125.00 | + | + | − | − | − |
| 250.00 | + | + | − | − | − |

In Table 1, "+" indicates that crystals were precipitated, "−" indicates that no crystals was precipitated, and "+/−" indicates that the solution was slightly turbid.

The modified hydrophobic excipient obtained in example 3 was not included in the experiment because the modified hydrophobic excipient crystallized out at room temperature, and the experimental results could not be directly observed by naked eyes.

According to the data comparison in table 1, the solubility of paclitaxel in examples 1,2 and 4 is greater than that in olive oil and castor oil, which indicates that the hydrophobic excipient has π-π function by introducing the substituent group with aromatic ring fluorene, which is beneficial to the aromatic ring accumulation between the hydrophobic excipients and the drug containing aromatic group. In addition, the carbamoyl group and amide group on the hydrophobic excipient can have non-covalent physical action with the drug through hydrogen bond, and the compatibility of the hydrophobic excipient and the hydrophobic drug can be improved through the above two additional molecular effects, thereby being beneficial to increasing the solubility of the drug.

Example 6

Blank, paclitaxel and docetaxel drug-loaded fat emulsions were prepared, and detected for the stability of the drug-loaded fat emulsion, which comprised the following steps:

Experiment 6.1

Blank fat emulsion: 1.5 mg of castor oil, 0.2 mg of egg yolk lecithin, 0.4 mg of mPEG2000-DSPE were dissolved in chloroform, blown to dry in nitrogen and dried under vacuum. Then 1 ml of phosphate buffer solution was added to adjust pH to 7.4, hydrated for 1 h, homogenized for 5 min at 20000 r/min with high speed shearing machine. The obtained blank fat emulsion was detected by Malvern ZS laser particle size analyzer, and the average particle size thereof was 200 nm.

Experiment 6.2

Paclitaxel-castor oil drug-loaded fat emulsion: 100 mg of paclitaxel, 300 mg of castor oil, 40 mg of egg yolk lecithin, and 80 mg of mPEG2000-DSPE were dissolved in chloroform, blown to dry in nitrogen and dried under vacuum. Then 20 ml of phosphate buffer solution was added to adjust pH to 7.4, hydrated for 1 h, homogenized for 5 min at 20000 r/min with high speed shearing machine. The obtained drug-loaded fat emulsion was detected by Malvern ZS laser particle size analyzer, and the average particle size thereof was 280 nm. The drug-loaded fat emulsion can be only stable for a short period of time after preparation, white precipitates began to appear after about 4 hours, and a large amount of white precipitates were formed after 12 hours.

Experiment 6.3

Docetaxel-castor oil drug-loaded fat emulsion: 100 mg of docetaxel, 300 mg of castor oil, 40 mg of egg yolk lecithin and 80 mg of mPEG2000-DSPE were taken and dissolved in chloroform, blown to dry in nitrogen and dried under vacuum. Then 20 ml of phosphate buffer solution was added to adjust pH to 7.4, hydrated for 1 h, homogenized for 5 min at 20000 r/min with high speed shearing machine. The obtained drug-loaded fat emulsion was detected by Malvern ZS laser particle size analyzer, and the average particle size thereof was 330 nm. The prepared drug-loaded emulsion had poor stability, white precipitates began to appear after about 1 hour, and a large amount of white precipitates appeared after 4 hours.

Experiment 6.4

Paclitaxel-hydrophobic excipient of example 1 drug-loaded fat emulsion: 100 mg of paclitaxel, 300 mg of hydrophobic excipient obtained in example 1, 40 mg of egg yolk lecithin, and 80 mg of mPEG2000-DSPE were dissolved in chloroform, blown to dry in nitrogen and dried under vacuum. Then 20 ml of phosphate buffer solution was added to adjust pH to 7.4, hydrated for 1 h, homogenized for 5 min at 20,000 r/min with high speed shearing machine. The obtained drug-loaded fat emulsion was detected by Malvern ZS laser particle size analyzer, and the average particle size thereof was 215 nm. And the drug-loaded fat emulsion can remain stable for about 72 h after being prepared, then a white precipitate began to appear.

Experiment 6.5

Docetaxel-hydrophobic excipient of example 1 drug-loaded fat emulsion: 100 mg of docetaxel, 320 mg of the hydrophobic excipient prepared in example 1, 40 mg of egg yolk lecithin and 80 mg of mPEG2000-DSPE were dissolved in chloroform, blown to dry in nitrogen and dried under vacuum. Then 1 ml of phosphate buffer solution was added to adjust pH to 7.4, hydrated for 1 h, homogenized for 5 min at 20,000 r/min with high speed shearing machine. The obtained drug-loaded fat emulsion was detected by Malvern ZS laser particle size analyzer, and the average particle size thereof was 225 nm. And the drug-loaded fat emulsion can remain stable for about 1 day after being prepared, then a white precipitate began to appear at about 19 h.

Experiment 6.6

Paclitaxel-hydrophobic excipient of example 2 drug loaded fat emulsion: 100 mg of paclitaxel, 300 mg of hydrophobic excipient prepared in example 2, 40 mg of egg yolk lecithin, and 80 mg of mPEG2000-DSPE were dissolved in chloroform, blown to dry in nitrogen and dried under vacuum. Then 20 ml of phosphate buffer solution was added to adjust pH to 7.4, hydrated in a 50° C. water bath for 1 h, homogenized for 5 min at 20,000 r/min with high speed shearing machine. The obtained drug-loaded fat emulsion was detected by Malvern ZS laser particle size analyzer, and the average particle size thereof was 215 nm. And the drug-loaded fat emulsion can remain stable for about 2 day after being prepared, then a white precipitate began to appear at about 76 h.

Experiment 6.7

Docetaxel-hydrophobic excipient of example 2 drug-loaded fat emulsion: 100 mg of docetaxel, 320 mg of the hydrophobic excipient prepared in example 4, 40 mg of egg yolk lecithin and 80 mg of mPEG2000-DSPE were dissolved in chloroform, blown to dry in nitrogen and dried under vacuum. Then 1 ml of phosphate buffer solution was added to adjust pH to 7.4, hydrated for 1 h, and homogenized for 5 min at 20,000 r/min with high speed shearing machine. The obtained drug-loaded fat emulsion was detected by Malvern ZS laser particle size analyzer, and the average particle size thereof was 210 nm. And the drug-loaded fat emulsion can remain stable for about 20 h after being prepared, then a white precipitate began to appear.

Experiment 6.8

Paclitaxel-hydrophobic excipient of example 3 drug loaded fat emulsion: 100 mg of paclitaxel, 300 mg of hydrophobic excipient prepared in example 3, and 40 mg of egg yolk lecithin, 80 mg of mPEG2000-DSPE were dissolved in chloroform, blown to dry in nitrogen and dried under vacuum. Then 20 ml of phosphate buffer solution was added to adjust pH to 7.4, hydrated in a 50° C. water bath for 1 h, homogenized for 5 min at 20,000 r/min with high speed shearing machine. The obtained drug-loaded fat emulsion was detected by Malvern ZS laser particle size analyzer, and the average particle size thereof was 235 nm. And the drug-loaded fat emulsion can remain stable for at least 2 day after being prepared, then a white precipitate began to appear at about 76 h.

Experiment 6.9

Docetaxel-hydrophobic excipient of example 3 drug-loaded fat emulsion: 100 mg of docetaxel, 320 mg of the hydrophobic excipient prepared in the example 3, 40 mg of egg yolk lecithin and 80 mg of mPEG2000-DSPE were dissolved in chloroform, blown to dry in nitrogen and dried under vacuum. Then 1 ml of phosphate buffer solution was added to adjust pH to 7.4, hydrated in a 50° C. water bath for 1 h, homogenized for 5 min at 20000 r/min with high speed shearing machine. The obtained drug-loaded fat emulsion was detected by Malvern ZS laser particle size analyzer, and the average particle size thereof was 220 nm. And the drug-loaded fat emulsion can remain stable for about 1 day and a half after being prepared, then a white precipitate began to appear at about 32 h.

Experiment 6.10

Docetaxel-hydrophobic excipient of example 4 drug-loaded fat emulsion: 100 mg of docetaxel, 320 mg of the hydrophobic excipient prepared in example 4, 40 mg of egg yolk lecithin and 80 mg of mPEG2000-DSPE were dissolved in chloroform, blown to dry in nitrogen and dried under vacuum. Then 1 ml of phosphate buffer solution was added to adjust pH to 7.4, hydrated for 1 h, homogenized for 5 min at 20,000 r/min with high speed shearing machine. The obtained drug-loaded fat emulsion was detected by Malvern ZS laser particle size analyzer, and the average particle size thereof was 210 nm. And the drug-loaded fat emulsion can be stable for about 22 h after being prepared, then a white precipitate began to appear.

According to the experimental result, when the castor oil is used as the oil phase, the drug-loaded fat emulsion prepared by the castor oil, the paclitaxel and the docetaxel is relatively unstable, and white precipitate is generated after about 1-4 h. When the modified hydrophobic excipient of the present application is used as an oil phase, the stability of the drug-loaded fat emulsion prepared by the modified hydrophobic excipient, paclitaxel and docetaxel generally can reach more than 20 h, which indicates that, forming the hydrophobic excipient by introducing an aromatic ring and a carbamoyl group or an amide group into a hydrophobic compound can provide the hydrophobic compound with a π-π function, thereby being beneficial for aromatic ring stacking between the hydrophobic excipient and the drug containing the aromatic group, so that they can combine with each other through non-covalent physical action. In addition, the carbamoyl group and the amide group can be combined with the drug in a non-covalent physical way through a hydrogen bond in a hydrophobic environment, so as to further improve the stability of the drug-loaded fat emulsion.

According to the experimental results, under the same conditions, the stability of the drug-loaded fat emulsion prepared from docetaxel is worse than that of the drug-loaded fat emulsion prepared from paclitaxel because docetaxel is more hydrophilic than paclitaxel.

According to the experimental result, the stability of the drug-loaded fat emulsion prepared from the modified hydrophobic excipient prepared from the hydrogenated castor oil is higher than that of the drug-loaded fat emulsion prepared from the modified hydrophobic excipient prepared from the castor oil, which indicates that adopting the hydrogenated castor oil as the raw material to prepare the hydrophobic excipient is beneficial to improve the stability of combination of hydrophobic excipient and the drug.

The examples of the specific embodiment are preferred examples of the present application, and the scope of the present application is not limited by these examples, so that all equivalent changes of the structure, shape and principle of the present application are covered by the protection scope of the present application.

What is claimed is:

1. A method for preparing a modified hydrophobic excipient, wherein the method comprises the following steps:

Step A. subjecting castor oil and N-tert-butoxycarbonylglycine acting as raw material, a dehydrating agent and a catalyst to an esterification reaction to generate intermediate I: castor oil-O—(N-t-butoxycarbonylglycine) triester, and adding an organic acid into the intermediate I, or performing catalytic hydrogenation to remove an amino protecting group of N-tert-butyloxycarbonyl, so as to generate intermediate II: castor oil-O-glycine triester;

a structural formula of intermediate I is as follows:

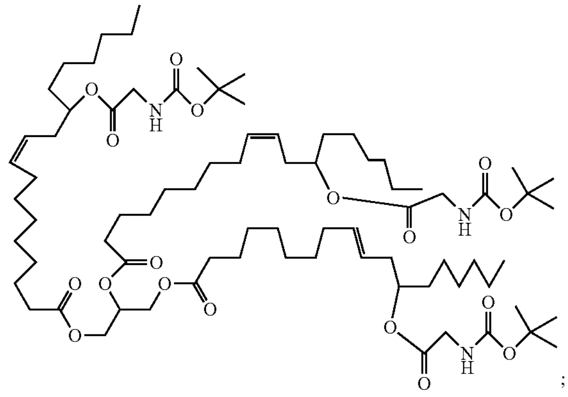 [SMILES: CCCCCCC(C/C=C\CCCCCCCC(=O)OCC(COC(=O)CCCCCCC/C=C/CC(CCCCCC)OC(=O)CNC(=O)OC(C)(C)C)OC(=O)CCCCCCC/C=C\CC(CCCCCC)OC(=O)CNC(=O)OC(C)(C)C)OC(=O)CNC(=O)OC(C)(C)C]

;

a structural formula of intermediate II is as follows:

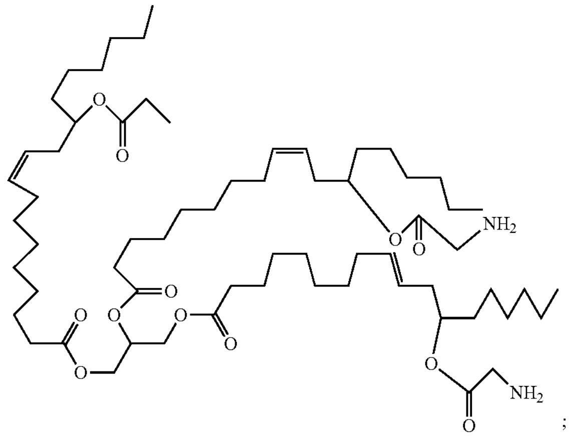 [SMILES: CCCCCCC(C/C=C\CCCCCCCC(=O)OCC(COC(=O)CCCCCCC/C=C/CC(CCCCCC)OC(=O)CN)OC(=O)CCCCCCC/C=C\CC(CCCCCC)OC(=O)CN)OC(=O)CC]

;

Step B. subjecting N-fluorenylmethoxycarbonyl-N'-tert-butoxycarbonyl-L-lysine and N-hydroxysuccinimide acting as raw material and a dehydrating agent to an esterification reaction to obtain intermediate III: N-fluorenylmethoxycarbonyl-N'-tertbutylcarbonyl-L-lysine-N-hydroxysuccinimide ester; and Step C. reacting the intermediate II and the intermediate III as raw material with an acid-binding agent under a dark condition to generate a modified hydrophobic excipient, a structural formula of the modified hydrophobic excipient is as follows:

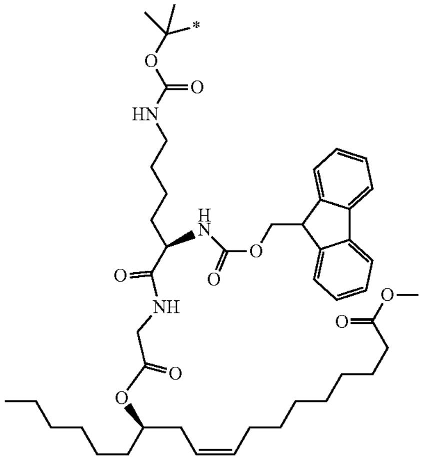

-continued

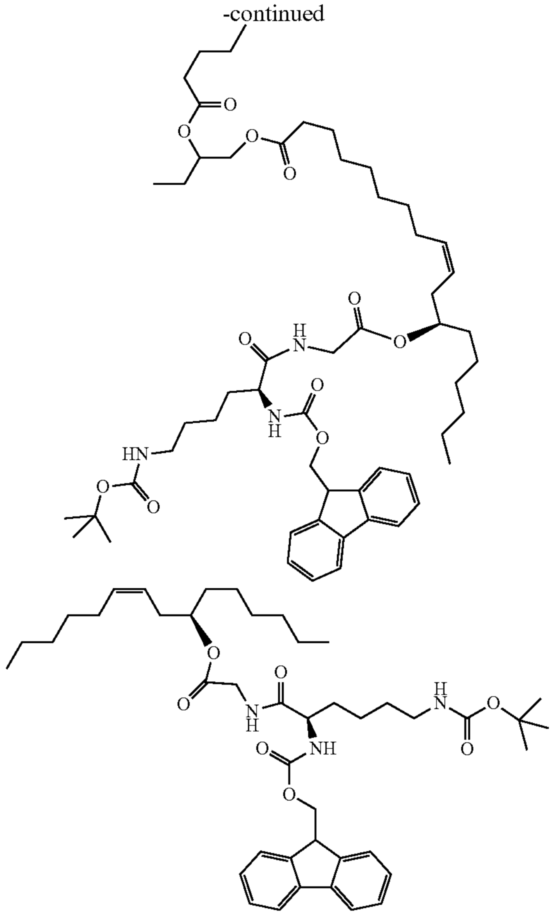

;

wherein, the dehydrating agent is dicyclohexylcarbodiimide, the catalyst is 4-dimethylaminopyridine or pyridine, the acid-binding agent is triethylamine, and the organic acid is trifluoroacetic acid.

2. The method according to claim 1, wherein, in Step A, the condition of the catalytic hydrogenation reaction is $H_2$ (1-5 atm) and Pt/C as catalyst.

3. The method according to claim 1, wherein, in Step A, the intermediate I is dissolved in a solvent before adding the acid or performing hydrogenation.

4. A stable drug-loaded fat emulsion, comprising a drug and the modified hydrophobic excipient prepared by the method according to claim 1 as an oil phase excipient.

5. The stable drug-loaded fat emulsion according to claim 4, wherein the drug-loaded fat emulsion is composed of the modified hydrophobic excipient, a hydrophobic drug and a surfactant, wherein the modified hydrophobic excipient, the hydrophobic drug and the surfactant are dissolved in a solvent, the solvent is removed, a buffer solution is added for hydration, and then the solution is prepared into the drug-loaded fat emulsion.

6. The stable drug-loaded fat emulsion according to claim 5, wherein a proportion of the modified hydrophobic excipient to the hydrophobic drug and the surfactant is 300 mg of the modified hydrophobic excipient, 0-150 mg of the hydrophobic drug, 40-450 mg of egg yolk lecithin, 0-225 mg of cholesterol and 0-300 mg of mPEG2000-DSPE.

7. The stable drug-loaded fat emulsion according to claim 4, wherein the drug loaded by the modified hydrophobic excipients comprises paclitaxel, and docetaxel.

8. The stable drug-loaded fat emulsion according to claim 4, wherein a method for preparing the drug-loaded fat emulsion comprises one or a combination of high-speed shearing, phase transition, high-pressure homogenization, micro-jet and micro-fluidic methods.

* * * * *